(12) United States Patent
Longo et al.

(10) Patent No.: US 8,916,556 B2
(45) Date of Patent: Dec. 23, 2014

(54) PHARMACEUTICAL FORMULATIONS COMPRISING NEUROTROPHIN MIMETICS

(75) Inventors: Frank M. Longo, Menlo Park, CA (US); Stephen M. Massa, Burlingame, CA (US)

(73) Assignees: The University of North Carolina at Chapel Hill, Chapel Hill, NC (US); The Regents of The University of California, Oakland, CA (US); The United States of America represented by the Department of Vetran Affairs, Washington, DC (US)

(*) Notice: Subject to any disclaimer, the term of this patent is extended or adjusted under 35 U.S.C. 154(b) by 628 days.

(21) Appl. No.: 12/762,947

(22) Filed: Apr. 19, 2010

(65) Prior Publication Data

US 2010/0267727 A1 Oct. 21, 2010

Related U.S. Application Data

(63) Continuation of application No. 11/396,936, filed on Apr. 3, 2006, now Pat. No. 7,723,328.

(60) Provisional application No. 60/671,785, filed on Apr. 15, 2005.

(51) Int. Cl.

| A61K 31/535 | (2006.01) |
|---|---|
| C07D 295/18 | (2006.01) |
| C07K 16/28 | (2006.01) |
| A61K 31/497 | (2006.01) |
| A61K 31/522 | (2006.01) |
| A61K 31/537 | (2006.01) |
| A61K 31/496 | (2006.01) |
| A61K 31/155 | (2006.01) |
| A61K 31/445 | (2006.01) |

(52) U.S. Cl.
CPC ........... *C07K 16/2878* (2013.01); *A61K 31/497* (2013.01); *A61K 31/522* (2013.01); *A61K 31/537* (2013.01); *A61K 31/496* (2013.01); *C07K 2316/96* (2013.01); *A61K 31/155* (2013.01); *A61K 31/445* (2013.01)
USPC ........................... 514/237.8; 544/168

(58) Field of Classification Search
USPC ........................... 514/237.8; 544/168
See application file for complete search history.

(56) References Cited

U.S. PATENT DOCUMENTS

| 4,743,607 A | 5/1988 | Jones et al. |
|---|---|---|
| 5,028,622 A | 7/1991 | Plaitakis |
| 5,321,029 A | 6/1994 | Maschler et al. |
| 5,439,806 A | 8/1995 | Kunz et al. |
| 5,608,067 A * | 3/1997 | Afonso et al. ............... 546/82 |
| 5,958,875 A | 9/1999 | Longo et al. |
| 6,017,878 A | 1/2000 | Saragovi et al. |
| 6,583,148 B1 | 6/2003 | Kelley et al. |
| 6,699,989 B1 | 3/2004 | Shetty |
| 6,881,719 B2 | 4/2005 | Saragovi et al. |
| 7,723,328 B2 | 5/2010 | Longo et al. |
| 2002/0051988 A1 | 5/2002 | Gilchrest et al. |
| 2004/0167183 A1 | 8/2004 | Klopfenstein et al. |
| 2004/0186044 A1 | 9/2004 | Cosgaya et al. |
| 2006/0246072 A1 | 11/2006 | Longo et al. |
| 2007/0060526 A1 | 3/2007 | Longo et al. |
| 2008/0221147 A1 | 9/2008 | Ross et al. |
| 2011/0003819 A1 | 1/2011 | Longo et al. |
| 2011/0230479 A1 | 9/2011 | Longo et al. |
| 2014/0100224 A1 | 4/2014 | Longo et al. |

FOREIGN PATENT DOCUMENTS

| DE | 199 39 910 | 3/2001 |
|---|---|---|
| EP | 0 386 611 A2 | 9/1990 |
| EP | 1 238 970 | 9/2002 |
| JP | 08119922 A * | 5/1996 |
| JP | H10-81661 | 3/1998 |
| WO | WO89/10744 | 11/1989 |
| WO | WO 96/16980 A1 | 6/1996 |
| WO | WO 97/42168 A1 | 11/1997 |
| WO | WO 98/07742 | 2/1998 |
| WO | WO 9837079 A1 * | 8/1998 |
| WO | WO 98/47863 A1 | 10/1998 |
| WO | WO98/54123 | 12/1998 |
| WO | WO 00/17190 A2 | 3/2000 |
| WO | WO00/27378 | 5/2000 |
| WO | WO 0037462 A1 * | 6/2000 |
| WO | WO01/00657 | 1/2001 |
| WO | WO01/14320 | 3/2001 |
| WO | WO01/90047 | 11/2001 |
| WO | WO 03/006423 A1 | 1/2003 |
| WO | WO 03/040096 A2 | 5/2003 |
| WO | WO 03/104226 A1 | 12/2003 |
| WO | WO 2004/028466 A2 | 4/2004 |
| WO | WO2004/031145 | 4/2004 |

(Continued)

OTHER PUBLICATIONS

Azaryan et al., "Synthesis and anticonvulsant activity of aminoalkyl derivatives of 5-(p-alkoxyphenyl)-5-methylhydantoins," Khim. Farm. Zhurnal 18(5):568-572 (1984).
Beattie, M.S. et al. (2002) Neuron 36, 375-386.
Cacace et al. Derivati degli acidi teofillin-7-carbonico, teofillin-7-acetico e teofillin-7-propionico. Annali di Chimica, vol. 45, (1955), pp. 983-993.
Carlson et al. Developing a dynamic pharmacophore model for HIV-1 integrase. Journal of Medicinal Chemistry, vol. 43, (2000), pp. 2100-2114.
Carter, B.D., et al. (2002) Science 272, 542-545.
Casaccia-Bonnefil, P., Carter, B.D., Dobrowsky, R.T., Chao, M.V. (1996) Nature 386, 716-719.
Fahnestock, M., Michalski, B., Xu, B., Coughlin, M.D. (2001) Mol Cell Neurosci 18, 210-220.
Foehr, E.D., et al. (2003) J Neurosci Res 73, 7556-7563.
Gentry, J.J., Casaccia-Bonnefil, P., Carter, B.D. (2000) J Biol Chem 275, 7558-7565.
Harrington, A.W, Kim, J.Y., Yoon, S.O. (2002) J Neurosci 22, 156-166.
Harrington, A.W. et al. (2004) Proc Natl Acad Sci USA 101, 6226-6230.
He, X.L., Garcia, K.C. (2004) Science 304, 870-875.
Huang, C.S. et al. (1994) J Biol Chem 274, 36707-36714.

(Continued)

*Primary Examiner* — Sarah Pihonak
(74) *Attorney, Agent, or Firm* — Jenkins, Wilson, Taylor & Hunt, P.A.

(57) ABSTRACT

Methods and compounds for treating neurodegenerative and other disorders. Included is the administering to a subject in need thereof an effective amount of a compound having binding specificity for a $p75^{NTR}$ receptor molecule. Enhanced survival of neural and other cells has been observed.

6 Claims, 10 Drawing Sheets

(56) References Cited

FOREIGN PATENT DOCUMENTS

| WO | WO 2004/077061 A1 | 9/2004 |
|---|---|---|
| WO | WO2005/044810 | 5/2005 |
| WO | WO2006/005941 | 1/2006 |
| WO | WO2006/113097 | 10/2006 |
| WO | WO 2008/107365 | 9/2008 |
| WO | WO2010/102212 | 9/2010 |

OTHER PUBLICATIONS

International Search Report and the Written Opinion of the International Searching Authority, or the Declaration corresponding to PCT Application No. PCT/US06/11985 dated Dec. 28, 2006.
Jaen et al., "Kynurenic acid derivatives inhibit the binding of nerve growth factor (NGF) to the low-affinity p75 NGF receptor," J. Med. Chem. 38(22):4439-4445 (1995).
Jakobs, "Communication pursuant to Article 94(3) EPC," 9 pages, Europe patent appl. No. 06758242.9, European Patent Office (Aug. 24, 2011).
Jakobs, "Communication," 10 pages, Europe patent appl. No. 06758242.9, European Patent Office (Aug. 23, 2010).
Kim, "International Search Report," 5 pages, International Patent Appl. No. PCT/US2010/026372, Korean Intellectual Property Office (mailed Jan. 31, 2011).
Kim, "Written Opinion of the International Searching Authority," 7 pages, International Patent Appl. No. PCT/US2010/026372, Korean Intellectual Property Office (mailed Jan. 31, 2011).
Lachyankar, M.B., et al. (2003) J Neurosci Res 71, 157-172.
Lad, S.P., Neet, K.E. (2003) J Neurosci Res 73, 614-626.
Lee, K.F. et al. (1992) Cell 69, 737-749.
Lee, R., Kermani, P., Teng, K.K., Hempstead, B.L. (2001) Science 294, 1945-1948.
Lin, Y.Z., Yao, S.Y., Veach, R.A., Torgerson, T.R., Hawiger, J. (1995) J Biol Chem 270, 14255-14258.
Longo et al. Neurotrophin-based strategies for neuroprotection. Journal of Alzheimer's Disease, vol. 6, (2004), pp. S13-S17.
Longo et al., "Small Molecule Modulation of p75 Neurotrophin Receptor Functions," CNS & Neurological Disorders—Drug Targets, vol. 7, pp. 63-70 (2008).
Longo, F.M. et al. (1999) J Neurosci Res 55, 230-237.
Longo, F.M., Manthorpe, M., Xie, Y.M., Varon, S. (1997) J Neurosci Res 48, 1-17.
Maliartchouk, S., Debeir, T., and Beglova, N. Cuello, A.C., Gehring, K, and Saragovi, H. U. (2000) J Biol Chem 275, 9946-9956.
Mamidipudi, V., Li, X., Wooten, M.W. (2002) J Biol Chem 277, 28010-28018.
Massa et al. Alzheimer's therapeutics. Journal of Molecular Neuroscience, vol. 19, (2002), pp. 107-111.
Massa et al. Alzheimer's therapeutics. Journal of Molecular Neuroscience, vol. 20, (2003), pp. 323-326.
Michaelis, M.L., Ansar, S., Chen, Y., Reiff, E.R., Seyb, K.I., Himes, R.H., Audus, K.L., and Georg, G.I. (2006) J Pharm Exp Ther 312:659-668.
Nykjaer, A. et al., (2004) Nature 427, 843-848.
Nykjaer, A., Willnow, T.E., and Petersen, C.M. (2005) Curr Opin Neurobiol 15, 49-57.
Oelssner, Pharmazie, 1961, vol. 16, pp. 84-89 (English abstract from CAS).
Oelssner, W. Zur pharmakologie neuartiger Methylxanthinderivate. Pharmazie, vol. 16, (1961), pp. 84-89.
Orazi et al., "Substitution in the hydantoin ring—I. Aminomethylation," Tetrahedron 15:93-99 (1961).
Partridge, W.M. (2002) Adv Exp Med Bio 513, 397-430).
Pihonak, "Office Action Summary," 19 pages, U.S. Appl. No. 11/396,936, United States Patent and Trademark Office (May 27, 2009).
Podulso, J.F., Curran, G.L. (1996) Brain Res Mol Brain Res 36, 280-286.
Roux, P.P., Bhakar, A.L., Kennedy, T.E., Barker, P.A. (2001) J Biol Chem 276, 23097-23104.
Sakurai, H., Chiba, H., Miyoshi, H., Sugita, T., Toriumi, W. (1999) J Biol Chem 274, 30353-30356.
Salehi, A.H., et al. (2000) Neuron 27, 279-288.
Saltzman, W.M., Mak, M.W., Mahoney, M.J., Duenas, E.T., Cleland, J.L. (1999) Pharm Res 16, 232-240.
Thoenen et. al., Nature Neuroscience Supplement, 2002, Nature Publishing Group, pp. 1046-1050.
Walsh, G.S., Krol, K.M., Kawaja, M.D. (1999) J Neurosci 19, 258-273.
Wang, J.J., Rabizadeh, S., Tasinato, A., Sperandio, S., Ye, X., Green, M., Assa-Munt, N., Spencer, D., and Bredesen, D.E. (2000) J Neurosci Res 60, 587-593.
Yang, T. et al. (2003) J Neurosci 23, 3353-3363.
Yankner, B.A., Caceres, A., Duffy, L.K. (1990) PNAS 87:9020-9023.
Yoon, S.O., Casaccia-Bonnefil, P., Carter, B., Chao, M.V. (1998) J Neurosci 18, 3273-3281.
Zhang, Y., et al. (2003) J Neurosci 23, 7385-7394.
Zhou, J., Holtzman, D.M., Weiner, R.I., Mobley, W.C. (1994) Proc Natl Acad Sci USA 91, 3824.
Zhou, J., Valletta, J.S., Grimes, M.L., Mobley, W.C. (1995) J Neurochem 65, 1146-1156.
Dechant, G., and Barde, Y., "The neurotrophin receptor $p75^{NTR}$: novel functions and implications for diseases of the nervous system," Nature Neuroscience. vol. 5, No. 11 pp. 1131-1136 (2002).
Interview Summary corresponding to U.S. Appl. No. 11/396,936 dated Aug. 25, 2009.
Klosa, "Synthesis of alkylenediamino amides of theophylline-7-acetic acid," Journal fusr Praktische Chemie (Leipzig). vol. 12 pp. 212-214 (1961) [Abstract].
Notice of Allowance corresponding to U.S. Appl. No. 11/396,936 dated Jan. 7, 2010.
Notification Concerning Transmittal of International Preliminary Report on Patentability (Chapter I of the Patent Cooperation Treaty) corresponding to PCT/US2006/011985 dated Oct. 25, 2007.
Notification Concerning Transmittal of International Preliminary Report on Patentability (Chapter I of the Patent Cooperation Treaty) corresponding to PCT/US2010/026372 dated Sep. 15, 2011.
Oelssner, Pharmazie. vol. 16 pp. 84-89 (1961) [Abstract].
Official Action corresponding to European Patent Application No. 06 758 242.9-1216 dated Jul. 9, 2012.
Official Action corresponding to Japanese Patent Application No. 2008-506498 dated Sep. 16, 2011.
Official Action corresponding to Japanese Patent Application No. 2008-506498 dated May 21, 2012.
Official Action corresponding to U.S. Appl. No. 11/396,936 dated Feb. 26, 2009.
Official Action corresponding to U.S. Appl. No. 12/762,940 dated Jul. 20, 2012.
Saragovi, H.U., and Burgess, K., "Small molecule and protein-based neurotrophic ligands: agonists and antagonists as therapeutic agents." Exp. Opin. Ther. Patents. vol. 9, No. 6 pp. 737-751 (1999).
Extended European Search Report corresponding to European Patent Application No. 06 758 242.91216 dated Aug. 23, 2010.
Massa et al., "Small, Nonpeptide $p75^{NTR}$ Ligands Induce Survival Signaling and Inhibit proNGF-Induced Death," The Journal of Neuroscience. vol. 26, No. 20 pp. 5288-5300 (2006).
Official Action corresponding to European Patent Application No. 06 758 242.9-1216 dated Aug. 24, 2011.
Official Action corresponding to U.S. Appl. No. 11/396,936 dated May 27, 2009.
Official Action corresponding to U.S. Appl. No. 12/910,349 dated Dec. 27, 2012.
LeSauteur et al., "Small Peptide Mimics of Nerve Growth Factor Bind the TrkA Receptors and Affect Biological Responses," The Journal of Biological Chemistry. vol. 270, No. 12 pp. 6564-6569 (1995).
Mufson, E.J., and Kordower, J.H., "Cortical neurons express nerve growth factor receptors in advanced age and Alzheimer's disease," PNAS. vol. 89 pp. 569-573 (1992).
Official Action corresponding to U.S. Appl. No. 12/910,349 dated Aug. 23, 2012.

(56) References Cited

OTHER PUBLICATIONS

Solthoff et al., "Nerve Growth Factor Promotes the Activiation of Phosphatidylinositol 3-Kinase and Its Association with the *trk* Tyrosine Kinase," The Journal of Biological Chemisty. vol. 267, No. 24 pp. 17472-17477 (1992).

Vetter et al., "Nerve growth factor rapidly stimulates tyrosine phosphorylation of phospholipase C-γ1 by a kinase activity associated with the product of the *trk* protooncogene," PNAS. vol. 88, No. 13 pp. 5650-5654 (1991).

Bronfman et al., "Ligand-Induced Internalization of the p75 Neurotrophin Receptor: A Slow Route to the Signaling Endosome," The Journal of Neuroscience. vol. 23, No. 8 pp. 3209-3220 (2003).

Domeniconi et al., "Pro-NGF secreted by astrocytes promotes motor neuron cell death," Mol. Cell Neurosci. vol. 34, No. 2 pp. 271-279 (2007).

Longo, F.M., and Massa, S.M., "Neuroprotective Strategies in Alzheimer's Disease," NeuroRx. vol. 1 pp. 117-127 (2004).

Longo et al., "Neurotrophin Small Molecule Mimetics: Candidate Therapeutic Agents for Neurological Disorders," Curr. Med. Chem.—CNS Agents. vol. 5 pp. 29-41 (2005).

Longo et al., "The in vitro biological effect of nerve growth factor is inhibited by synthetic peptides," Cell Regulation. vol. 1 pp. 189-195 (1990).

Official Action corresponding to U.S. Appl. No. 12/762,940 dated Oct. 25, 2012.

Pehar et al., "Modulation of $p75^{NTR}$-dependent motor neuron death by a small non-peptidyl mimetic of the neurotrophin loop 1 domain," European Journal of Neuroscience. vol. 24, No. 6 pp. 1575-1580 (2006).

Thoenen, H., and Sendtner, M., "Neurotrophins: from enthusiastic expectations through sobering experiences to rational therapeutic approaches," Nature Neuroscience. Supplement 5 pp. 1046-1050 (2002).

Wong et al., "A $p75^{NTR}$ and Nogo receptor complex mediates repulsive signaling by myelin-associated glycoprotein," Nature Neuroscience. vol. 5, No. 12 pp. 1302-1308 (2002).

Zhang, Y., and Partridge, W.M., "Neuroprotection in Transient Focal Brain Ischemia After Delayed Intravenous Administration of Brain-Derived Neurotrophic Factor Conjugated to a Blood-Brain Barrier Drug Targeting System," Stroke. vol. 32, No. 6 pp. 1378-1384 (2001).

Extended European Search Report corresponding to European Patent Application No. 12 191 674.6-1453 dated Mar. 28, 2013.

Extended European Search Report corresponding to European Patent Application No. 12 191 676.1-1453 dated Apr. 19, 2013.

Extended European Search Report corresponding to European Patent Application No. 10749395.9-1462 dated Apr. 28, 2014.

Official Action corresponding to European Patent Application No. 12 191 674.6-1453 dated Mar. 18, 2014.

Official Action corresponding to European Patent Application No. 12 191 676.1-1453 dated Mar. 19, 2014.

Official Action corresponding to Japanese Patent Application No. 2012-220523 dated Jan. 20, 2014.

Official Action corresponding to Japanese Patent Application No. 2012-220524 dated Mar. 31, 2014.

Official Action corresponding to Japanese Patent Application No. 2011-553135 dated Apr. 7, 2014.

\* cited by examiner

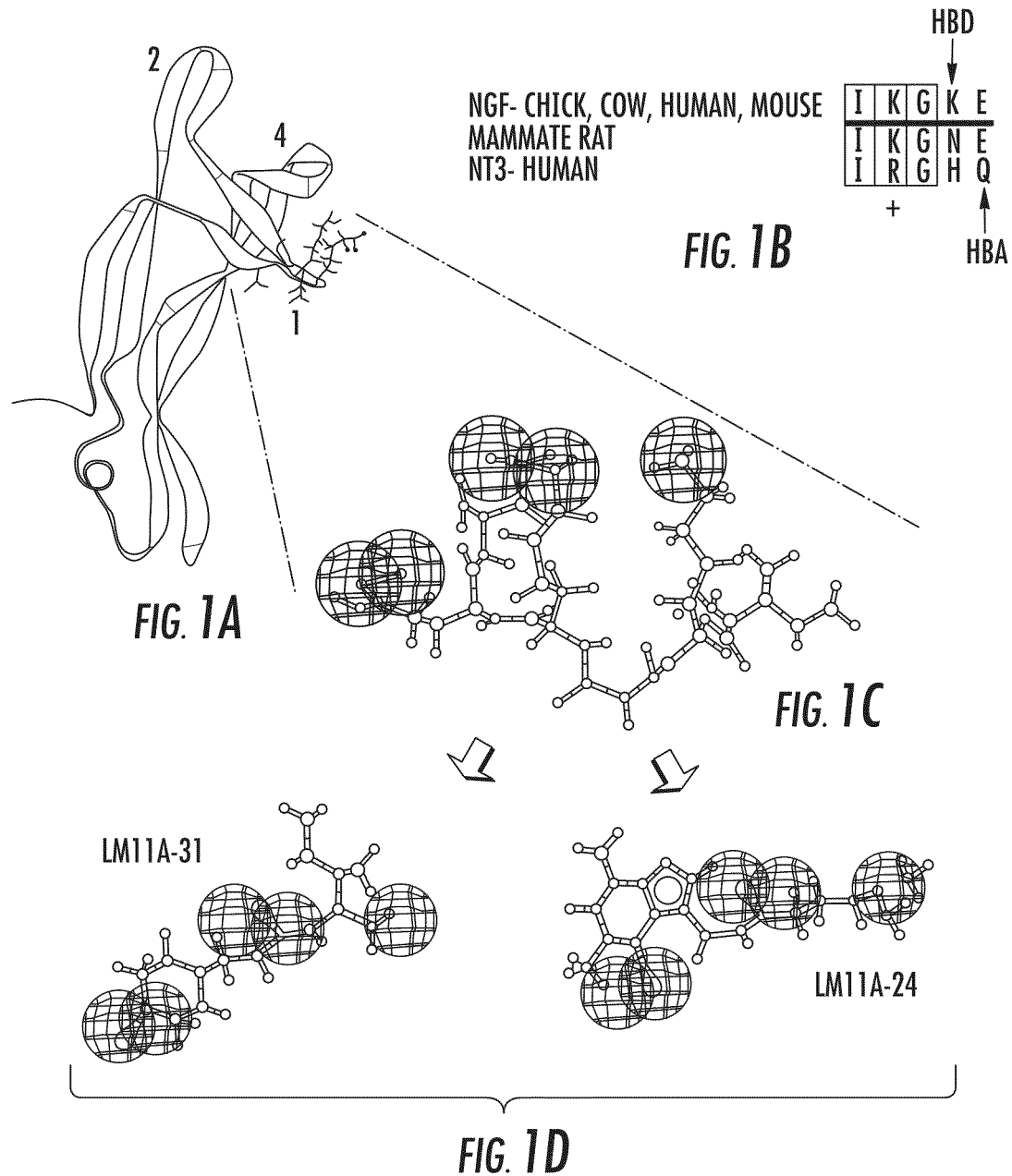

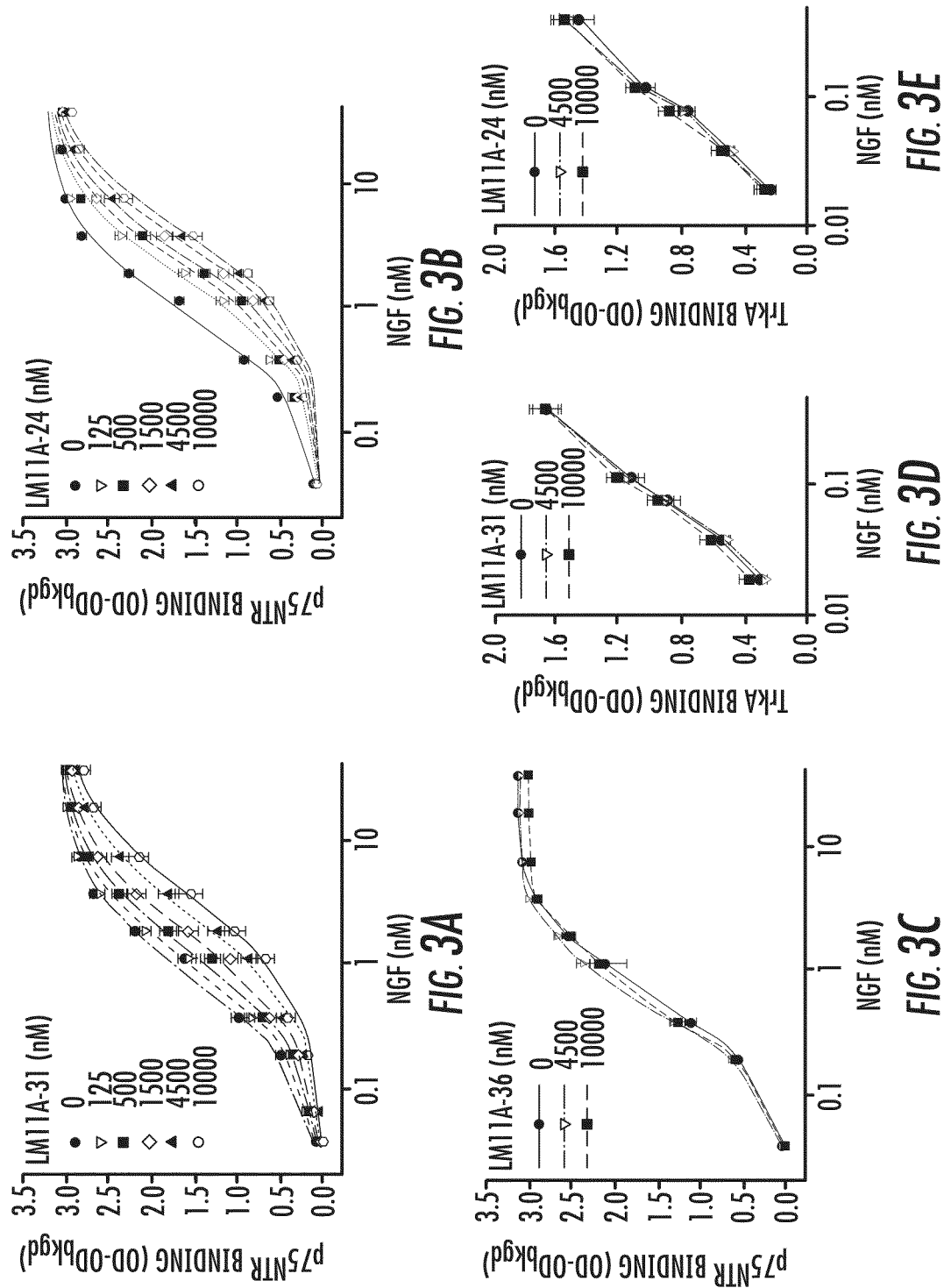

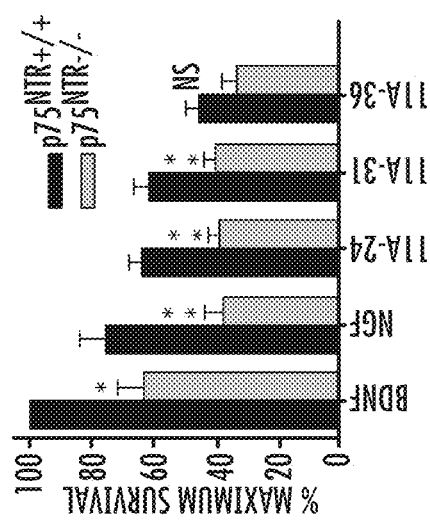
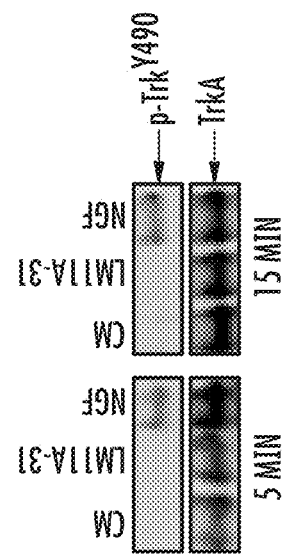
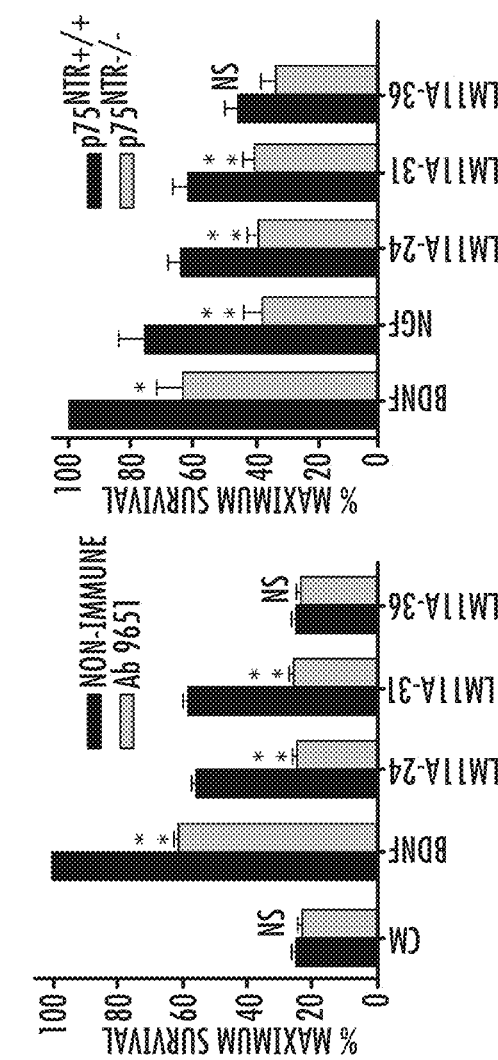
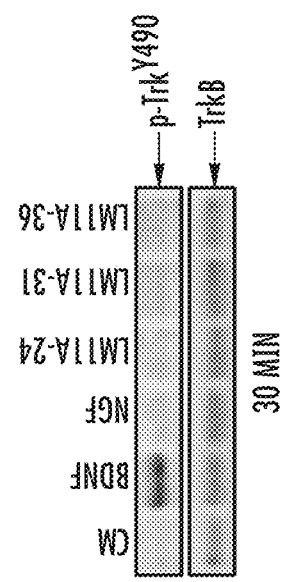
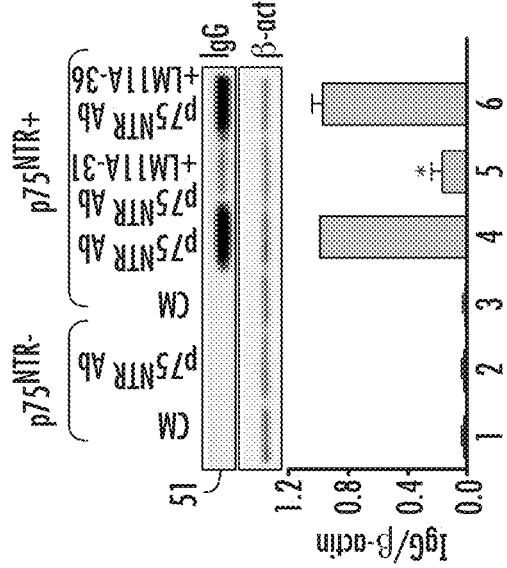

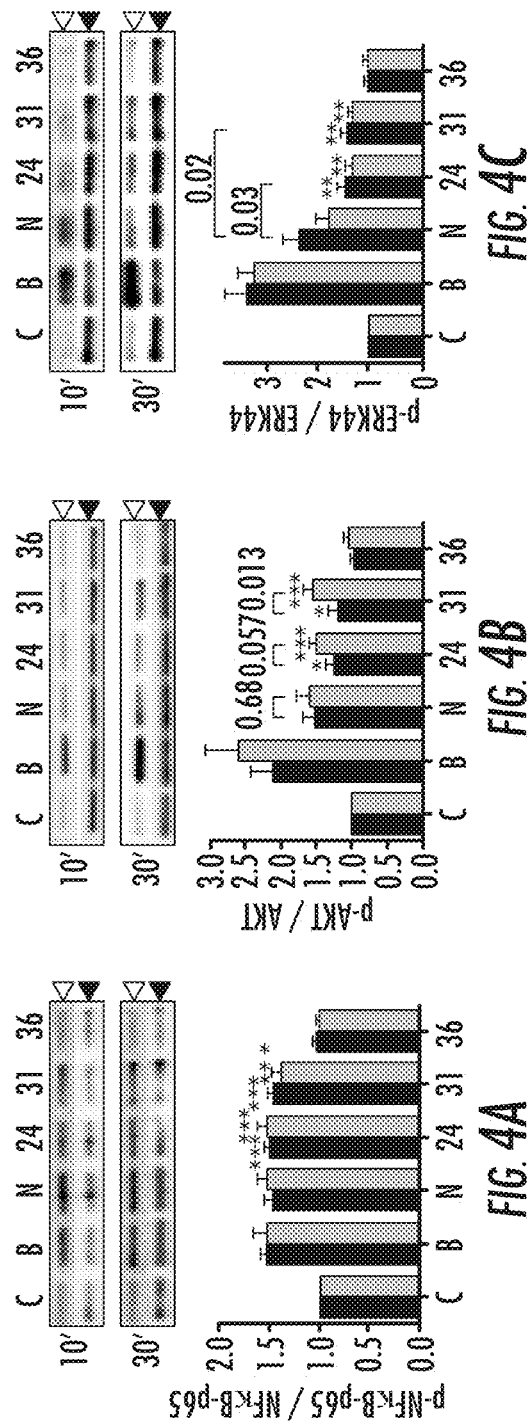

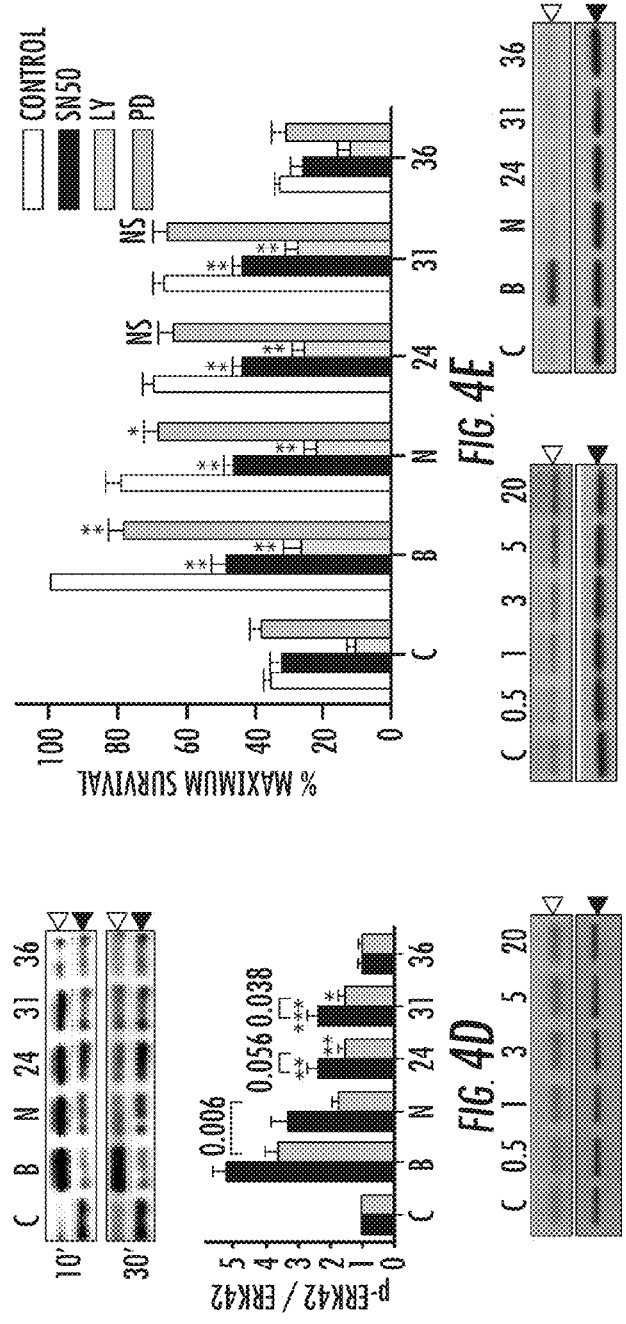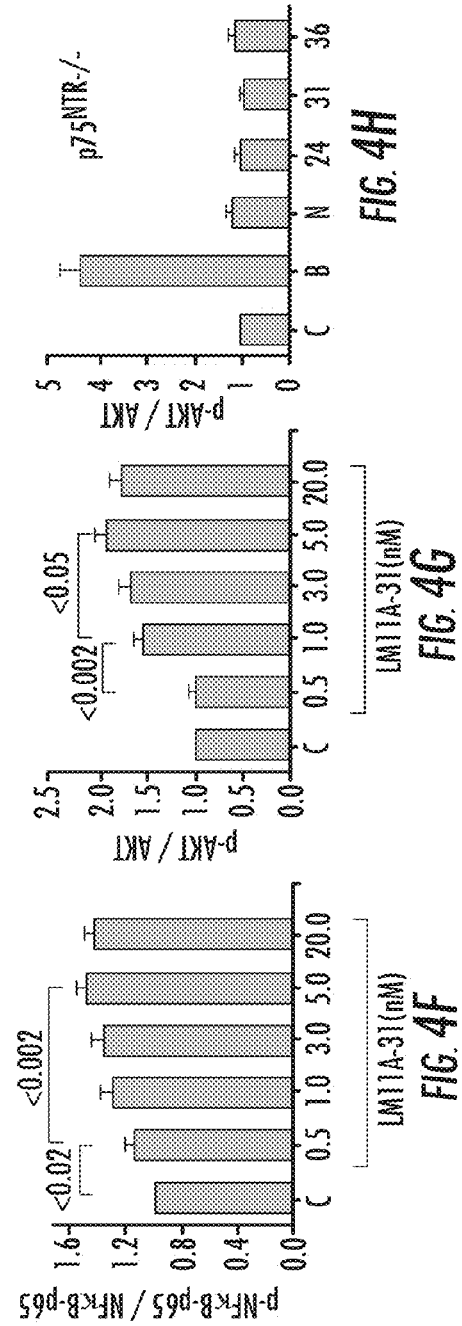

SEQUENCE LISTING

```
<160> NUMBER OF SEQ ID NOS: 3

<210> SEQ ID NO 1
<211> LENGTH: 5
<212> TYPE: PRT
<213> ORGANISM: Homo sapiens

<400> SEQUENCE: 1

Ile Lys Gly Lys Glu
1               5

<210> SEQ ID NO 2
<211> LENGTH: 5
<212> TYPE: PRT
<213> ORGANISM: Rattus sp.

<400> SEQUENCE: 2

Ile Lys Gly Asn Glu
1               5

<210> SEQ ID NO 3
<211> LENGTH: 5
<212> TYPE: PRT
<213> ORGANISM: Homo sapiens

<400> SEQUENCE: 3

Ile Arg Gly His Gln
1               5
```

PHARMACEUTICAL FORMULATIONS COMPRISING NEUROTROPHIN MIMETICS

CROSS REFERENCE TO RELATED APPLICATIONS

This application is a continuation of U.S. patent application Ser. No. 11/396,936, filed on Apr. 3, 2006 now U.S. Pat. No. 7,723,328, herein incorporated by reference in its entirety, which is based on and claims priority to U.S. Provisional Application Ser. No. 60/671,785, filed Apr. 15, 2005, herein incorporated by reference in its entirety.

GRANT STATEMENT

This invention was made with government support under Grant No. NS030687 awarded by the National Institutes of Health. The government has certain rights in the invention.

TECHNICAL FIELD

The presently disclosed subject matter generally relates to the treatment of neurodegenerative and other disorders in a subject. More particularly, the methods of the presently disclosed subject matter relate to administering to a subject an effective amount of a compound having binding specificity for a $p75^{NTR}$ receptor molecule to treat a neurodegenerative or other disorder in the subject.

TABLE OF ABBREVIATIONS

2—D two-dimensional
3—D three-dimensional
Aβ—amyloid-β
Ab—antibody
AD—Alzheimer's disease
BCA—bicinchoninic acid
BDNF—brain-derived neurotrophic factor
b.i.d.—twice daily
cm—centimeter
d—day
D—Dalton
DMEM—Dulbecco's Modified Eagle Media
ECL—electrogenerated chemiluminescence
EDTA—ethylenediamine tetraacetic acid
ELISA—Enzyme Linked ImmunoSorbent Assay
ERK—extracellular signal-regulated protein kinase
FBS—fetal bovine serum
g—gram
h—hour
HBA—hydrogen bond acceptor
HBD—hydrogen bond donor
HEPES—4-2-hydroxyethyl-1-piperazineethanesulfonic acid
HRP—horseradish peroxidase
IgG—Immunoglobin G
IP—Intraperitoneal
IV—intravenous
$K^{32}$—lysine residue number 32
kcal—kilocalorie
kg—kilogram
MBP—myelin basic protein
mg—milligram
min—minute
ml—milliliter
mM—millimolar
mol—mole
MTT—3-(4,5-dimethylthiazol-2-yl)-2,5-diphenyltetrazolium bromide
MW—molecular weight
NaCl—sodium chloride
ng—nanogram
nM—nanomolar
NS—not significant
NMR—nuclear magnetic resonance
NGF—nerve growth factor
nM—nanomolar
P—probability
$p75^{NTR}$—neurotrophin receptor
PBS—phosphate-buffered saline
pmol—picomole
PMSF—phenylmethylsulfonyl fluoride
PO—per os (by mouth)
pro-NGF—unprocessed precursor of NGF
PVDF—Polyvinylidine Difluoroide
SDS—sodium dodecyl sulfate
SE—standard error
s.e.m.—standard error of measurement
Tris—2-Amino-2-(hydroxymethyl)-1,3-propanediol
TUNEL—Terminal deoxynucleotidyl transferase-mediated deoxyuridine triphosphate nick-end labeling
μg—microgram
μl—microliter
μM—micromolar
%—percent
° C.—degrees Celsius
≥—greater than or equal to
>—greater than
≤—less than or equal to
<—less than

BACKGROUND

Neurotrophins are polypeptides that play a role in the development, function, and/or survival of certain cells, including neurons, oligodendrocytes. Schwann cells, hair follicle cells, and other cells. The death or dysfunction of neurons and other cell types has been directly implicated in a number of neurodegenerative disorders. It has been suggested that alterations in neurotrophin localization, expression levels of neurotrophins, and/or expression levels of the receptors that bind neurotrophins are therefore linked to neuronal degeneration. Degeneration occurs in the neurodegenerative disorders Alzheimer's. Parkinson's and ALS, among others. Degeneration of oligodendrocytes can occur in central nervous system injury, multiple sclerosis, and other pathological states.

A variety of neurotrophins have been identified, including Nerve Growth Factor (NGF), Neurotrophin-3 (NT-3), Neurotrophin-4/5 (NT-4/5), Neurotrophin 6 (NT-6) and Brain Derived Neurotrophic Factor (BDNF). Neurotrophins are found in both precursor form, known as pro-neurotrophins, and in mature form. The mature forms are proteins of about 120 amino acids in length that exist in physiological states as stable, non-covalent approximately 25 kDa homodimers. Each neurotrophin monomer includes three solvent-exposed β-hairpin loops, referred to as loops 1, 2, and 4 that exhibit relatively high degrees of amino acid conservation across the neurotrophin family.

Mature neurotrophins bind preferentially to the receptors Trk and $p75^{NTR}$, while pro-neurotrophins, which contain an N-terminal domain proteolytically removed in mature forms, interact principally with the $p75^{NTR}$ receptor and through their N-terminal domains, with the sorting receptor sortilin (Fahnestock, M., Michalski, B., Xu, B., Coughlin, M. D. (2001) *Mol Neurosci* 18, 210-220; Harrington, A. W. et al. (2004) *Proc Natl Acad Sci USA* 101, 6226-6230; Nyklaer, A. et al., (2004) *Nature* 427, 843-848). The p75$^{NTR}$ receptor interacts with Trks and modulates Trk signaling, but is also independently coupled to several signaling systems, including pro-survival signals, IRAK/TRAF6/NFκB. P13/AKT, and pro-apoptotic signals, NRAGE/JNK (Mamidipudi, V., Li, X., Wooten, M. W. (2002) *J Biol Chem* 277, 28010-28018; Roux, P. P., Bhakar, A. L., Kennedy. T. E. Barker, P. A. (2001) *J Biol Chem* 276, 23097-23104; Salehi, A. H., et al. (2000) *Neuron* 27, 279-288).

When administered for therapeutic use, neurotrophins exhibit suboptimal pharmacological properties, including poor stability with low serum half lives, likely poor oral bioavailability, and restricted central nervous system penetration (Podulso, J. F., Curran, G. L. (1996) *Brain Res Mol Brain Res* 36, 280-286; Saltzman, W. M., Mak, M)., Mahoney, M. J., Duenas, E. T., Cleland, J. L. (1999) *Pharm Res* 16, 232-240; Partridge, W. M. (2002) *Adv Exp Med Bio* 513, 397-430). Additionally, the highly pleiotropic effects of neurotrophins achieved through action of the dual receptor signaling network increases the chances of adverse effects.

It has been suggested that the unliganded form of p75$^{NTR}$ is proapoptofic, and that homodimerization induced by neurotrophin binding eliminates the effect (Wang, J. J., Rabizadeh, S., Tasinato, A., Sperandio, Ye, X., Green, M., Assa-Munt, N., Spencer, D., and Bredesen, D. E. (2000) *J Neurosci Res* 60, 587-593), consistent with studies showing no effects on survival of monomeric p75$^{NTR}$ ligands, including monovalent Fabs (Maliartchouk, S., Debeir, T., and Beglova, N. Cuello, A. G., Gehring, K. and Saragovi, H. U. (2000) *J Biol Chem* 275, 9946-9956) and monomeric cyclic peptides (Longo, F. M., Manthorpe, M., Xie, Y. M., Varon, S. (1997) *J Neurosci Res* 48, 1-17), while related bivalent forms in each study promote cell survival. However, these monomeric ligands may not engage the receptor in the same way as the natural ligands. Though active NGF is a homodimers containing 2 potential p75$^{NTR}$ binding sites, recent structural evidence suggests that it engages only one p75$^{NTR}$ molecule, disallowing the binding of another (He, X. L., Garcia, K. C. (2004) *Science* 304, 870-875).

Unfortunately, technical and ethical considerations have thus far hampered the development of therapeutic agents based upon neurotrophins. For example, it is technically difficult to produce sufficient quantities of pure neurotrophins using recombinant DNA techniques. Additionally, although it is possible to utilize human fetal cells to produce neurotrophins, the ethical ramifications raised by the use of such cells (typically obtained from an aborted fetus) have all but prevented the utilization of this approach. Accordingly, there is an unmet need in the art for the development of small molecule agents with favorable drug-like features based upon neurotrophins that are capable of targeting specific neurotrophin receptors for use in the treatment of disorders or diseases.

SUMMARY

Disclosed herein are methods of treating a neurodegenerative or other disorder in a subject, comprising administering to the subject an effective amount of a compound having binding specificity for a p75$^{NTR}$ receptor molecule.

Also disclosed herein are methods of facilitating neural, oligodendrocyte, or other cell survival comprising treating such cells with a compound having binding specificity for a p75$^{NTR}$ receptor molecule.

Additionally disclosed herein are compounds having binding specificity for a p75$^{NTR}$ receptor molecule.

In some embodiments, the neurodegenerative disorder is selected from the group consisting of Alzheimer's disease, Huntington's disease, amyotrophic lateral sclerosis, epilepsy. Parkinson's disease, Pick's disease, spinal cord injury, stroke, hypoxia, ischemia, brain injury, diabetic neuropathy, peripheral neuropathy, nerve transplantation, multiple sclerosis, peripheral nerve injury, hair loss, and other conditions involving degeneration or dysfunction of cells expressing p75.

In some embodiments, the subject is a human subject.

In some embodiments, the compound having binding specificity for a p75$^{NTR}$ receptor molecule is a mimetic of a neurotrophin β-turn loop.

In some embodiments, the compound comprises a pharmacophore substantially identical to the pharmacophore illustrated in FIG. 1c.

In some embodiments, the compound is a small molecule or a peptide.

In some embodiments, the compound is selected from the group consisting of:

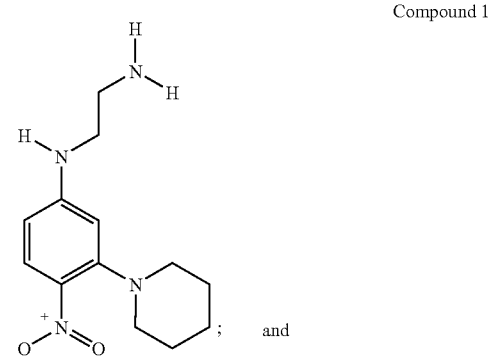

Compound 1

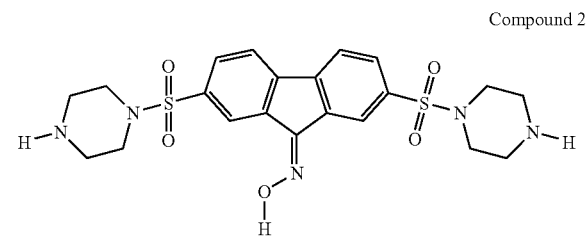

Compound 2

In some embodiments, the compound is selected from the group consisting of a compound of Formula (I-II):

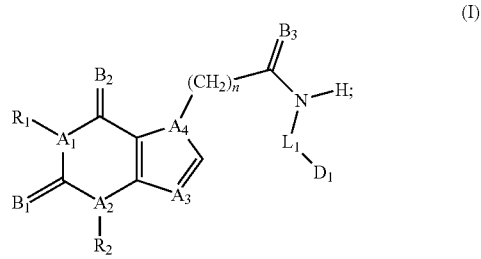

(I)

-continued

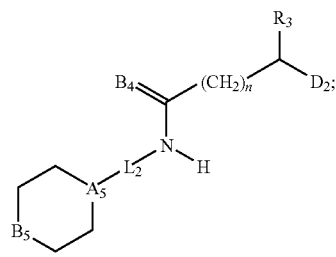

(II)

wherein:

n is an integer from 0 to 8;

L₁ and L₂ are a linking group selected from the group consisting of alkylene, substituted alkylene, cycloalkyl, substituted cycloalkyl, cycloalkene, substituted cycloalkene, aryl, substituted aryl, alkenylene, and substituted alkenylene;

R₁, R₂, and R₃ are each independently selected from the group consisting of H, alkyl, substituted alkyl, cycloalkyl, halo, cyano, nitro, mercapto, hydroxyl, alkoxyl, aryl, aryloxyl, substituted aryl, and aralkyloxyl;

A₁, A₂, A₃, A₄, and A₅ are each independently selected from the group consisting of N and CH;

B₁, B₂, B₃, B₄, and B₅ are each independently selected from the group consisting of O, S, and NR₄, wherein R₄ is selected from the group consisting of H, alkyl, substituted alkyl, cycloalkyl, aryl, and substituted aryl; and D₁ and D₂ are selected from the group consisting of:

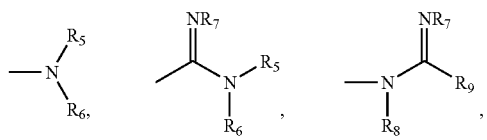

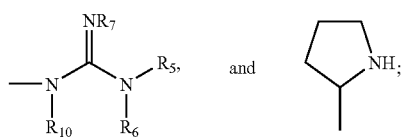

wherein:

each R₅, R₆, R₈, R₉, and R₁₀ is independently selected from the group consisting of H, alkyl, substituted alkyl, cycloalkyl, aryl, substituted aryl, aralkyl, hydroxyalkyl, hydroxycycloalkyl, alkoxycycloalkyl, aminoalkyl, acyloxyl, alkylaminoalkyl, and alkoxycarbonyl;

each R₇ is independently selected from the group consisting of H, hydroxyl, alkyl, substituted alkyl, aryl, substituted aryl, acyloxyl, and alkoxyl; or R₇ and R₅ or R₇ and R₉ together represent a C₂ to C₁₀ alkyl, C₂ to C₁₀ hydroxyalkyl, or O₂ to C₁₀ alkene;

or a pharmaceutically acceptable salt thereof.

In some embodiments, L₁ and L₂ are each independently —(CH₂)ₘ—, wherein m is an integer from 1 to 8.

In some embodiments, the compound of Formula (I) has the following structure:

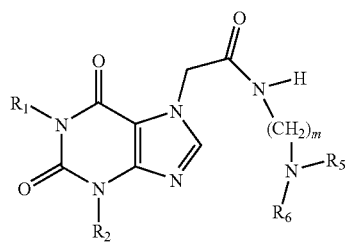

wherein:

m is an integer from 1 to 8;

R₁ and R₂ are each independently selected from the group consisting of H, alkyl, substituted alkyl, cycloalkyl, aryl, aryloxyl, substituted aryl, and aralkyloxyl; and R₅ and R₆ are each independently selected from the group consisting of H, alkyl, substituted alkyl, cycloalkyl, aryl, substituted aryl, aralkyl, hydroxyl, alkoxyl, hydroxyalkyl, hydroxycycloalkyl, alkoxycycloalkyl, aminoalkyl, acyloxyl, alkylaminoalkyl, and alkoxycarbonyl.

In some embodiments, the compound of Formula (I) has the following structure:

Compound 3

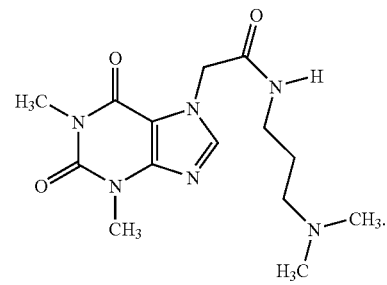

In some embodiments, the compound of Formula (II) has the following structure:

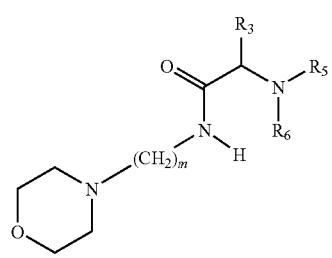

wherein:

m is an integer from 1 to 8;

R₃ is selected from the group consisting of H, alkyl, substituted alkyl, cycloalkyl, halo, hydroxyl, alkoxyl, aryl, aryloxyl, substituted aryl, and aralkyloxyl; and R₅ and R₆ are each independently selected from the group consisting of H, alkyl, substituted alkyl, cycloalkyl, aryl, substituted aryl, aralkyl, hydroxyl, alkoxyl, hydroxyalkyl, hydroxycycloalkyl, alkoxycycloalkyl, aminoalkyl, acyloxyl, alkylaminoalkyl, and alkoxycarbonyl.

In some embodiments, the compound of Formula (II) has the following structure:

Compound 4

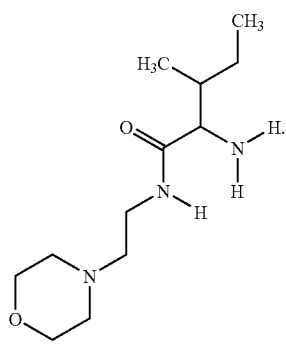

In some embodiments, the neurotrophin is a nerve growth factor (NGF).

In some embodiments, the β-turn loop is loop 1 of the NGF.

In some embodiments, the compound has the formula:

Compound 7

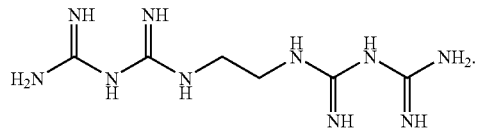

In some embodiments, the compound has binding specificity for a neurotrophin binding site of the $p75^{NTR}$ receptor molecule.

In some embodiments, the compound comprises a derivative of a parent compound having binding specificity for a $p75^{NTR}$ receptor molecule, wherein the derivative also has binding specificity for the $p75^{NTR}$ receptor.

In some embodiments, the derivative exhibits an enhancement in at least one of the characteristics selected from the group consisting of hydrophilicity, lipophilicity, amphipathicity, solubility, bioavailability, and resistance to hepatic degradation, as compared to the parent compound.

In some embodiments, the compound is selected from the group consisting of a compound of Formula (I-II):

(I)

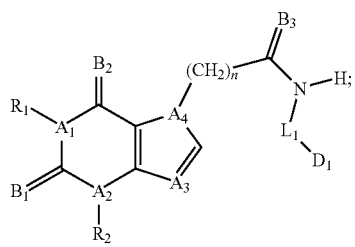

(II)

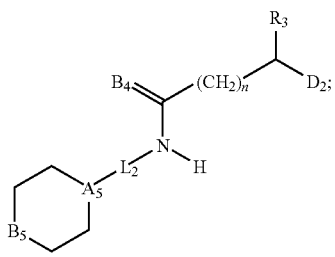

wherein:

n is an integer from 0 to 8;

$L_1$ and $L_2$ are a linking group selected from the group consisting of alkylene, substituted alkylene, cycloalkyl, substituted cycloalkyl, cycloalkene, substituted cycloalkene, aryl, substituted aryl, alkenylene, and substituted alkenylene;

$R_1$, $R_2$, and $R_3$ are each independently selected from the group consisting of H, alkyl, substituted alkyl, cycloalkyl, halo, cyano, nitro, mercapto, hydroxyl, alkoxyl, aryl, aryloxyl, substituted aryl, and aralkyloxyl;

$A_1$, $A_2$, $A_3$, $A_4$, and $A_5$ are each independently selected from the group consisting of N and CH;

$B_1$, $B_2$, $B_3$, $B_4$, and $B_5$ are each independently selected from the group consisting of O, S, and $NR_4$, wherein $R_4$ is selected from the group consisting of H, alkyl, substituted alkyl, cycloalkyl, aryl, and substituted aryl; and $D_1$ and $D_2$ are selected from the group consisting of:

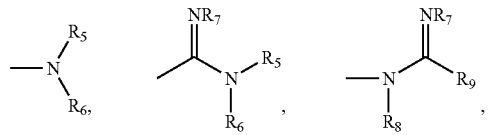

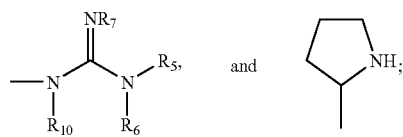

wherein:

each $R_5$, $R_6$, $R_8$, $R_9$, and $R_{10}$ is independently selected from the group consisting of H, alkyl, substituted alkyl, cycloalkyl, aryl, substituted aryl, aralkyl, hydroxyalkyl, hydroxycycloalkyl, alkoxycycloalkyl, aminoalkyl, acyloxyl, alkylaminoalkyl, and alkoxycarbonyl;

each $R_7$ is independently selected from the group consisting of H, hydroxyl, alkyl, substituted alkyl, aryl, substituted aryl, acyloxyl, and alkoxyl; or $R_7$ and $R_5$ or $R_7$ and $R_9$ together represent a $O_2$ to $C_{10}$ alkyl, $O_2$ to $C_{10}$ hydroxyalkyl, or $C_2$ to $C_{10}$ alkene;

or a pharmaceutically acceptable salt thereof, subject to the proviso that the compound of Formula (I) is not:

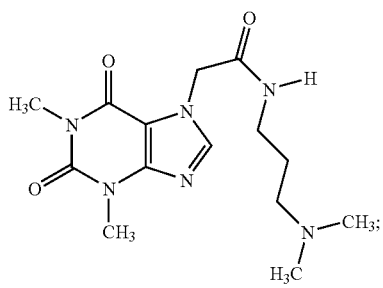

Compound 3 and
the compound of Formula (II) is not

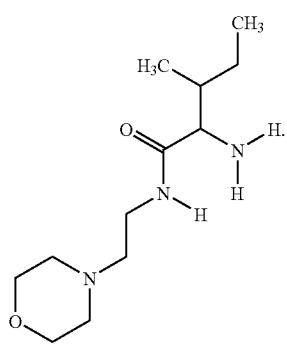

Compound 4

An object of the presently disclosed subject matter is to provide methods of facilitating cell survival using neurotrophin mimetics.

An object of the presently disclosed subject matter having been stated hereinabove, and which is addressed in whole or in part by the present presently disclosed subject matter, other objects will become evident as the description proceeds when taken in connection with the accompanying examples and drawings as best described hereinbelow.

BRIEF DESCRIPTION OF THE DRAWINGS

FIG. 1a is a ribbon representation of the X-ray crystal structure of human NGF with β-turn loops 1, 2, and 4 designated. The average side chain positions for loop 1 are illustrated.

FIG. 1b represents the comparison of peptide sequences (SEQ ID NOs: 1-3) of loop 1 from NGF and NT3 from the indicated species and the assignment of pharmacophores. Positively ionizable groups are signified by "+". "HBD" and "HBA" represent hydrogen bond donor and hydrogen bond acceptor, respectively.

FIG. 1c shows application of the pharmacophoric features to a 3D loop model. Hydrogen bonding features are represented by pairs of spheres with their relative positions indicating the locations of the acceptor and the donor. One of the spheres of the pair is centered on putative acceptor/donor features in the model, while the other indicates the target location of a complementary feature on any potentially interacting molecule. The diameter of the spheres represents the spatial tolerance for chemical feature matching in 3D conformer library scans.

FIG. 1d is a 3D loop model disclosing representative fits to the pharmacophore of two compounds identified by application of the novel pharmacophore in library screening subsequently found to be active as disclosed herein.

FIG. 3a is a series of NGF/p75$^{NTR}$-Fc binding curves, in the presence of increasing concentrations of Compound 4, as detected by NGF ELISA. Symbols are mean+/−s.e.m. n≥10 for all determinations. Lines represent fitting to a modified Gaddum/Schild equation, with an overall $R^2$ value of 0.93 for Compound 4. Also, P<0.0001 by ANOVA with post-hoc Bonferroni/Dunn testing, for comparisons between binding curves at 0 nM compound and curves with >500 nM Compound 4. $K_D$ for NGF in the absence of compounds was 0.8-0.9 nM, consistent with previous reports of approximately 1 nM (Nykiaer, A. et al. (2004) *Nature* 427, 843-848). The symbols "●", "▽", "■", "◇", "▲", and "○" represent Compound 4 concentrations of zero, 125, 500, 1,500, 4,500, and 10,000 nanomolar, respectively.

FIG. 3b is a series of NGF/p75$^{N111}$-Fc binding curves, in the presence of increasing concentrations' of Compound 3, as detected by NGF ELISA. Symbols are mean+/−s.e.m. n≥10 for all determinations. Lines represent fitting to a modified Gaddum/Schild equation, with an overall $R^2$ value of 0.96 for Compound 3. Also, P<0.0001 by ANOVA with post-hoc Bonferroni/Dunn testing, for comparisons between binding curves at 0 nM compound and curves with ≥125 nM Compound 3. $K_D$ for NGF in the absence of compounds was 0.8-0.9 nM, consistent with previous reports of approximately 1 nM (Nykjaer, A. et al., (2004)*Nature* 427, 843-848). The symbols "●", "▽", "■", "▲" and "○" represent Compound 3 concentrations of zero, 125, 500, 1,500, 4,500, and 10,000 nanomolar, respectively.

FIG. 3c is a series of NGF/TrkA-Fc binding curves in the presence of increasing concentrations of Compound 5, showing no significant effect up to 10,000 nM. Symbols are mean+/−s.e.m. n≥10 for all determinations. The symbols "●", "▽", and "■", represent Compound 5 concentrations of zero, 4,500, and 10,000 nanomolar, respectively.

FIG. 3d is a series of NGF/TrkA-Fc binding curves in the presence of increasing concentrations of Compound 4 showing no compound effects up to 10,000 nM. Symbols are mean+/−s.e.m. n≥4 for all determinations. The symbols "●", "∇", and "■", represent Compound 4 concentrations of zero, 4,500, and 10,000 nanomolar, respectively.

FIG. 3e is a series of NGF/TrkA-Fc binding curves in the presence of increasing concentrations of Compound 3 showing no compound effects up to 10,000 nM. Symbols are mean+/−s.e.m. n≥4 for all determinations. The symbols "●", "∇", and "■", represent Compound 3 concentrations of zero, 4,500, and 10,000 nanomolar, respectively.

FIG. 3f is a digital image of a western blot showing displacement of anti-$p75^{NTR}$ Ab 9651 from anti-$p75^{NTR}$-expressing 3T3 cells by Compound 4, but not Compound 5. The upper panel represents IgG heavy chain, the lower panel represents β-actin. The graph represents quantitation. The bars represent mean+/−s.e.m., normalized to bound antibody (lane 4). n=4 for each condition. A single asterisk (*) represents P<0.0005, for comparison with binding in the absence of compound, by Student t-test. Antibody and compound treatments are designated above each lane. Ab 9651 did not bind to $p75^{NTR}$-negative cells (lanes 1 and 2). Ab 9651 bound to $p75^{NTR}$-positive cells (lane 4) and was significantly displaced by Compound 4 (lane 5), while Compound 5 had no effect (lane 6).

FIG. 3g is a bar graph showing that Ab 9651 has no effect on baseline survival (CM), partially inhibits BDNF, and completely inhibits Compound 3 and Compound 4 promotion of hippocampal neuron survival. The solid bars represent non-immune serum treatment. The shaded bars represent Ab 9651 treatment. The bars represent mean+/−s.e.m. n≥26 for each condition. Double asterisks (**) represent P<0.00001 (for comparisons between Ab 9651 and non-immune). NS represents not significant by Student t-test. Survival in the presence of BDNF Ab 9651 is shown to be significantly greater than CM+Ab 9651 (P<0.00001), while the differences between CM and Compounds 3, 4, and 5 in the presence of antibody are not significant.

FIG. 3h is a bar graph showing that $p75^{NTR}$-deficiency partially inhibits BDNF and completely inhibits NGF. Compound 3, and Compound 4 promotion of hippocampal neuron survival. Neurotrophins were applied at 1.8 nM, and compounds 5 nM. The solid bars represent $p75^{NTR+/+}$ cells. The shaded bars represent $P75^{NTR-/-}$ cells. The bars represent mean+/−s.e.m. n≥5 for each condition. The single asterisk (*) represents P<0.05, the double asterisk (**) represents P<0.005. NS represents not significant (for comparisons between knockout and wild type) by Student t-test. In $p75^{NTR-/-}$ cultures, BDNF treatment produced greater survival than NGF (P<0.05) or Compounds 3-5 (P<0.01). There was no significant difference in baseline survival between the genotypes.

FIG. 3i shows digital images of western blots of hippocampal neuron cultures using anti-phosphorylated $Trk^{Y490}$, compared with total TrkB. BDNF activated TrkB, while NGF and Compounds 3-5 resulted in no detectable activation at 10 or 30 minutes.

FIG. 3j shows digital images of western blots of TrkA-expressing 3T3 cells using anti-phosphorylated $Trk^{Y490}$ compared with total TrkA. NGF is shown to activate TrkA, while Compound 4 produced no detectable activation. Results of two additional independent assays for TrkB and TrkA activation were identical.

FIGS. 4a-4d are digital images of western blots of extracts of hippocampal cultures treated with culture media (C), BDNF (B) at 50 ng/ml, NGF (N) at 50 ng/ml, or Compounds 3-5 at 20 nM showing representative bands corresponding to phosphorylated signaling factors (open arrowheads) and the corresponding total factor (filled arrowheads) and quantitation of the ratio of phospho- to total factor, indicating degree of activation. Bars indicate mean+/−s.e.m. Solid bars represent sampling at 10 minutes. Shaded bars represent sampling at 30 minutes. n=6 independent blots for each determination. Single asterisks (*) represent P<0.001 for comparison with CM by Student t-test. Other comparisons are as indicated, with P values by Student t-test indicated above each bracket.

FIG. 4a is a digital image of a western blot indicating NFκB-p65 activation analysis, showing similar activation kinetics for all biologically active treatments.

FIG. 4b is a digital image of a western blot representing AKT activation analysis, showing a small lag in activation by the active compounds relative to NGF.

FIG. 4c is a digital image of a western blot representing ERK44 activation analysis, showing less activation at 10 minutes for the compounds relative to NGF.

FIG. 4d is the digital image of a western blot representing ERK42 activation analysis, showing prolonged activation with BDNF treatment relative to NGF and Compounds 3-5.

FIG. 4e is a bar graph indicating survival of hippocampal neurons in cultures treated with signaling pathway inhibitors and BDNF (25 ng/ml), NGF (25 ng/ml), or Compounds 3-5 (5 nM), showing substantial inhibition by NFκB and P13K pathway inhibitors, small effects of ERK inhibition on BDNF and NGF activity, and no effect of ERK inhibition on the activity of Compounds 3-5. SN50 is an NFκB translocation inhibitor. LY represents LY294002, a P13K inhibitor. PD represents PD98059, an ERK inhibitor. n=18 for each bar, showing mean+s.e.m. NS represents that the data is not significant. A single asterisk (*) indicates P<0.05, double asterisks (**) indicates that P<0.001 for comparison with control (no inhibitor) in each group. The open, solid, lighter-shaded, and darker-shaded bars represent control, SN50, LY, and PD, respectively.

FIG. 4f is the digital image of a western blot of signaling activation analysis of NFκB pathway activation. Bars indicate mean+/−s.e.m. n≥6 for each condition. P values are as indicated. Activation is detected between 0 and 0.5 nM for NFκB, reaching a plateau level at 5 nM.

FIG. 4g is the digital image of a western blot of signaling activation analysis of AKT pathway activation. Bars indicate mean+/−s.e.m. n≥6 for each condition. P values are as indicated. Activation is detected between 0.5 and 1 nM for AKT, reaching a plateau level at 5 nM.

FIG. 4h is the digital image of a western blot indicating AKT activation by growth factors and compounds in $p75^{NTR-/-}$ cells. n≥9 for each condition. There are no significant differences between culture medium alone and NGF or Compounds 3-5.

DETAILED DESCRIPTION

Figure 2A:
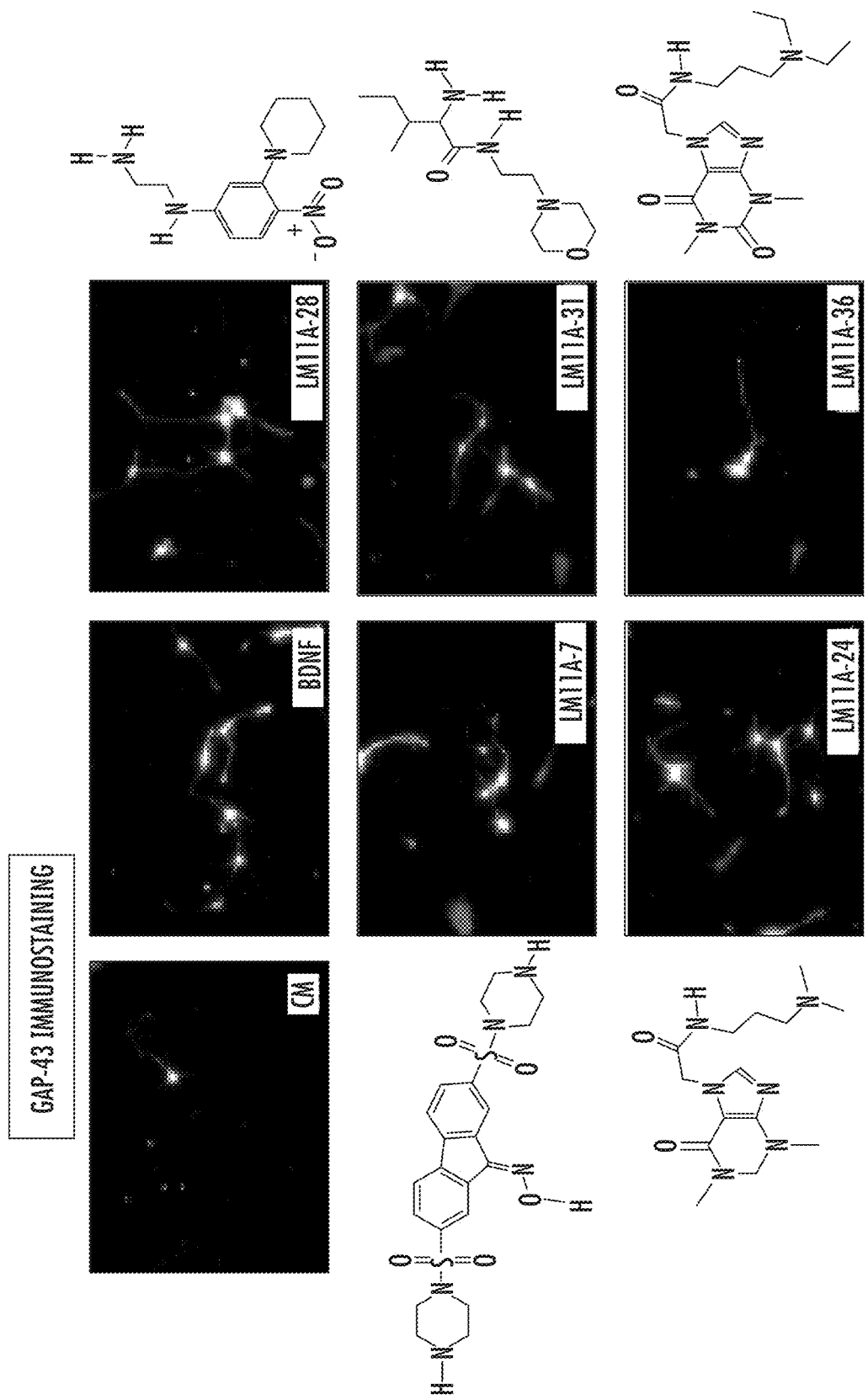
FIG. 2a is a series of fluorescence photomicrographs of E16-17 mouse hippocampal neuronal cultures treated with culture medium only (CM) or medium containing BDNF or Compounds I (referred to in the figures as "LM11A-28" or "28"), 2 (referred to in the figures as "LM11A-7" or "7"), 3 (referred to in the figures as "LM11A-24" or "24"), 4 (referred to in the figures as "LM11A-31" or "31"), or 5 (referred to in the figures as "LM11A-36" or "36"). The cultures were stained for expression of the neuron-specific, growth-associated protein GAP43 at 48 hours post treatment. The 2D structure of each compound is located adjacent to each image.
Figure 2B:
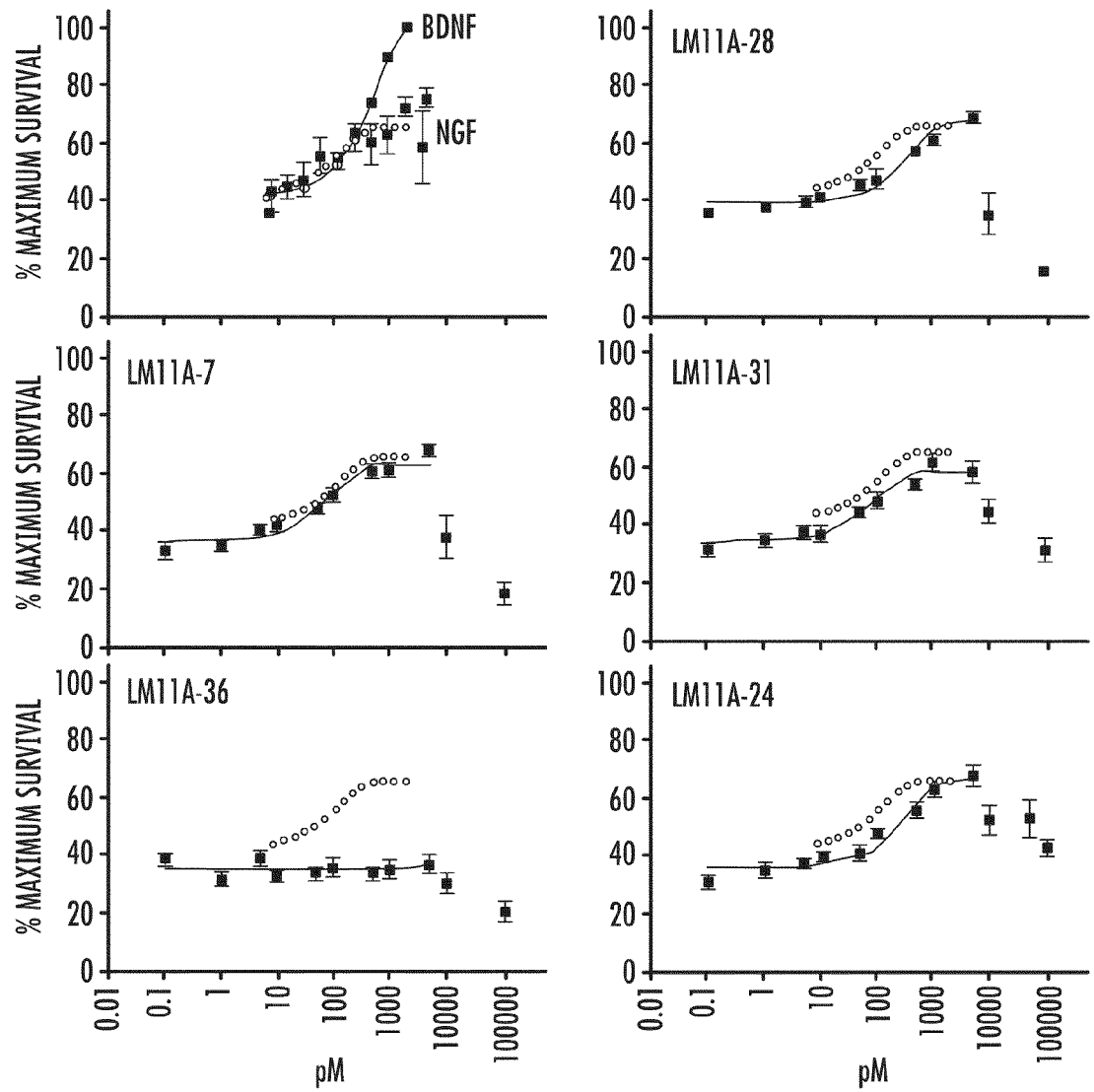
FIG. 2b is a series of neuron survival dose-response curves of BDNF, NGF, and Compounds 1-5, showing similar potency and maximal responses between NGF and Compounds 1-4 up to 5 nM, with no response to Compound 5. BDNF has similar potency, but a higher maximal response. Each of Compounds 1-5 show a decrementing response above 5 nM. Survival was determined as the total number of cells in each well that were both morphologically intact and filled with blue formazan MU-conversion product (Longo, F. M., Manthorpe, M., Xie, Y. M., and Varon, S. (1997) *J Neurosci Res* 48, 1-17). Counts were normalized to survival achieved with 25 ng/ml BDNF or to baseline survival. n is 4-18 for all determinations. Symbols and bars indicate mean+/−s.e.m., and lines are fits of a single exponential rise model to the data. Dotted lines in each graph represent the fitted NGF response.

In subjects with neurodegenerative and other disorders, alterations in neurotrophin localization, expression levels of neurotrophins, expression levels of the receptors that bind neurotrophins, and/or receptor signaling and functional outcomes can occur. Accordingly, by providing subjects suffering from such disorders with a corresponding neurotrophic factor or mimetic thereof that modulates p75$^{NTR}$ function or proNGF/NGF binding to prevent cellular degeneration or dysfunction, such neural degeneration can be alleviated or prevented. As disclosed for the first time herein, methods of treating neurodegenerative and other disorders and/or facilitating cell survival by administering a compound having binding specificity for p75$^{NTR}$ receptor molecule are provided.

The methods and compounds of the presently disclosed subject matter relate to compounds having binding specificity for a p75$^{NTR}$ receptor molecule. As used herein, discovery by in silico screening of compounds having binding specificity for p75$^{NTR}$ receptor are suitable for positively regulating survival of neural and other cells. Particularly, in cells showing trophic responses to neurotrophins or cells expressing p75$^{NTR}$ either constitutively or in response to injury or disease, the compounds promote survival signaling. In cells susceptible to neurotrophin-induced death, the compounds do not induce apoptosis, but inhibit neurotrophin-mediated death.

I. DEFINITIONS

It is to be understood that the terminology used herein is for the purpose of describing particular embodiments only and is not intended to be limiting.

Unless defined otherwise, all technical and scientific terms used herein have the same meaning as commonly understood to one of ordinary skill in the art to which the presently disclosed subject matter belongs. Although any methods and materials similar or equivalent to those described herein can be used in the practice or testing of the presently disclosed subject matter, representative methods and materials are herein described.

Following long-standing patent law convention, the terms "a", "an", and "the" refer to "one or more" when used in this application, including the claims. Thus, for example, reference to "a carrier" includes mixtures of one or more carriers, two or more carriers, and the like.

Unless otherwise indicated, all numbers expressing quantities of ingredients, reaction conditions, and so forth used in the specification and claims are to be understood as being modified in all instances by the term "about". Accordingly, unless indicated to the contrary, the numerical parameters set forth in the present specification and attached claims are approximations that can vary depending upon the desired properties sought to be obtained by the presently disclosed subject matter.

The term "about", as used herein when referring to a measurable value such as an amount of weight, time, dose, etc. is meant to encompass in one example variations of ±20% or ±10%, in another example ±5%, in another example ±1%, and in yet another example ±0.1% from the specified amount, as such variations are appropriate to perform the disclosed method.

As used herein, the term "neurodegenerative disorder" includes any disorder characterized by neural damage and include the following, without limitation, Alzheimer's disease, Huntington's disease, Pick's disease, amyotrophic lateral sclerosis, epilepsy. Parkinson's disease, spinal cord injury, stroke, hypoxia, ischemia, brain injury, diabetic neuropathy, peripheral neuropathy, nerve transplantation, multiple sclerosis, peripheral nerve injury, conditions involving degeneration or dysfunction of cells expressing p75 and other conditions involving degeneration of p75$^{NTR}$-expressing cells, such as hair loss.

As used herein the term "alkyl" refers to $C_{1\text{-}20}$ inclusive, linear (i.e., "straight-chain"), branched, or cyclic (a "cycloalkyl"), saturated or at least partially and in some cases fully unsaturated (i.e., alkenyl and alkynyl) hydrocarbon chains, including for example, methyl, ethyl, propyl, isopropyl, butyl, isobutyl, tert-butyl, pentyl, hexyl, octyl, ethenyl, propenyl, butenyl, pentenyl, hexenyl, octenyl, butadienyl, propynyl, methylpropynyl, butynyl, pentynyl, hexynyl, heptynyl, and allenyl groups. "Branched" refers to an alkyl group in which a lower alkyl group, such as methyl, ethyl or propyl, is attached to a linear alkyl chain. "Lower alkyl" refers to an alkyl group having 1 to about 8 carbon atoms (i.e., a $C_{1\text{-}8}$ alkyl), e.g., 1, 2, 3, 4, 5, 6, 7, or 8 carbon atoms. "Higher alkyl" refers to an alkyl group having about 10 to about 20 carbon atoms, e.g., 10, 11, 12, 13, 14, 15, 16, 17, 18, 19, or 20 carbon atoms. In certain embodiments, "alkyl" refers, in particular, to $C_{1\text{-}8}$ straight-chain alkyls. In other embodiments, "alkyl" refers, in particular, to $C_{1\text{-}8}$ branched-chain alkyls.

Alkyl groups can optionally be substituted (a "substituted alkyl") with one or more alkyl group substituents, which can be the same or different. The term "alkyl group substituent" includes but is not limited to alkyl, substituted alkyl, halo, arylamino, acyl, hydroxyl, aryloxyl, alkoxyl, alkylthio, arylthio, aralkyloxyl, aralkylthio, carboxyl, alkoxycarbonyl, oxo, and cycloalkyl. There can be optionally inserted along the alkyl chain one or more oxygen, sulfur or substituted or unsubstituted nitrogen atoms, wherein the nitrogen substituent is hydrogen, lower alkyl (also referred to herein as "alkylaminoalkyl"), or aryl.

Thus, as used herein, the term "substituted alkyl" includes alkyl groups, as defined herein, in which one or more atoms or functional groups of the alkyl group are replaced with another atom or functional group, including for example, alkyl, substituted alkyl, halogen, aryl, substituted aryl, alkoxyl, hydroxyl, nitro, amino, alkylamino, dialkylamino, sulfate, and mercapto.

Further, as used herein, the terms alkyl and/or "substituted alkyl" include an "allyl" or an "allylic group." The terms "allylic group" or "allyl" refer to the group —CH$_2$HC═CH$_2$ and derivatives thereof formed by substitution. Thus, the terms alkyl and/or substituted alkyl include allyl groups, such as but not limited to, allyl, methylallyl, di-methylallyl, and the like. The term "allylic position" or "allylic site" refers to the saturated carbon atom of an allylic group. Thus, a group, such as a hydroxyl group or other substituent group, attached at an allylic site can be referred to as "allylic."

The term "aryl" is used herein to refer to an aromatic substituent that can be a single aromatic ring, or multiple aromatic rings that are fused together, linked covalently, or linked to a common group, such as, but not limited to, a methylene or ethylene moiety. The common linking group also can be a carbonyl, as in benzophenone, or oxygen, as in diphenylether, or nitrogen, as in diphenylamine. The term "aryl" specifically encompasses heterocyclic aromatic compounds. The aromatic ring(s) can comprise phenyl, naphthyl, biphenyl, diphenylether, diphenylamine and benzophenone, among others. In particular embodiments, the term "aryl" means a cyclic aromatic comprising about 5 to about 10 carbon atoms, e.g., 5, 6, 7, 8, 9, or 10 carbon atoms, and including 5- and 6-membered hydrocarbon and heterocyclic aromatic rings.

The aryl group can be optionally substituted (a "substituted aryl") with one or more aryl group substituents, which can be the same or different, wherein "aryl group substituent" includes alkyl, substituted alkyl, aryl, substituted aryl, aralkyl, hydroxyl, alkoxyl, aryloxyl, aralkyloxyl, carboxyl, acyl, halo, nitro, alkoxycarbonyl, aryloxycarbonyl, aralkoxycarbonyl, acyloxyl, acylamino, aroylamino, carbamoyl, alkylcarbamoyl, dialkylcarbamoyl, arylthio, alkylthio, alkylene, and —NR'R", wherein R' and R" can each be independently hydrogen, alkyl, substituted alkyl, aryl, substituted aryl, and aralkyl.

Thus, as used herein, the term "substituted aryl" includes aryl groups, as defined herein, in which one or more atoms or functional groups of the aryl group are replaced with another atom or functional group, including for example, alkyl, substituted alkyl, halogen, aryl, substituted aryl, alkoxyl, hydroxyl, nitro, amino, alkylamino, dialkylamino, sulfate, and mercapto.

Specific examples of aryl groups include, but are not limited to, cyclopentadienyl, phenyl, furan, thiophene, pyrrole, pyran, pyridine, imidazole, benzimidazole, isothiazole, isoxazole, pyrazole, pyrazine, triazine, pyrimidine, quinoline, isoquinoline, indole, carbazole, and the like.

A structure represented generally by a formula such as:

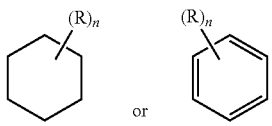

as used herein refers to a ring structure, for example, but not limited to a 3-carbon, a 4-carbon, a 5-carbon, a 6-carbon, and the like, aliphatic and/or aromatic cyclic compound comprising a substituent R group, wherein the R group can be present or absent, and when present, one or more R groups can each be substituted on one or more available carbon atoms of the ring structure. The presence or absence of the R group and number of R groups is determined by the value of the integer n. Each R group, if more than one, is substituted on an available carbon of the ring structure rather than on another R group. For example, the structure:

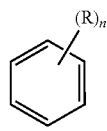

wherein n is an integer from 0 to 2 comprises compound groups including, but not limited to:

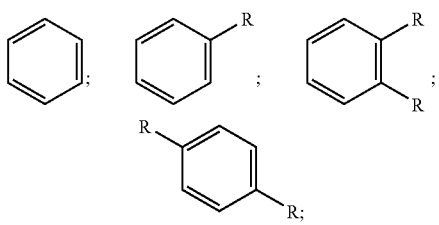

and the like.

The structure:

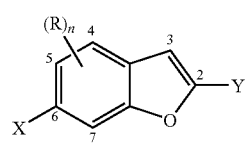

wherein n is one (1) comprises compound groups including:

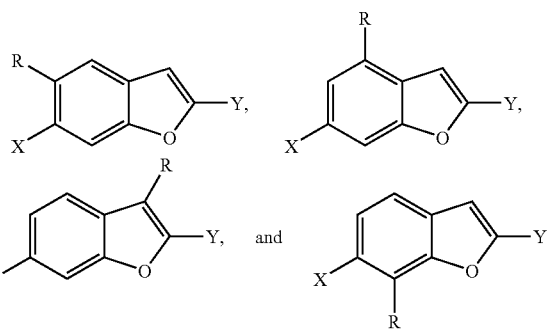

wherein the one (1) R substituent can be attached at any carbon on the benzofuran parent structure not occupied by another designated substituent, as in this case carbon 6 is substituted by X and carbon 2 is substituted by Y.

A dashed line representing a bond in a cyclic ring structure indicates that the bond can be either present or absent in the ring. That is a dashed line representing a bond in a cyclic ring structure indicates that the ring structure is selected from the group consisting of a saturated ring structure, a partially saturated ring structure, and an unsaturated ring structure.

In some embodiments, the compounds described by the presently disclosed subject matter contain a linking group. As used herein, the term "linking group" comprises a chemical moiety which is bonded to two or more other chemical moieties to form a stable structure. Representative linking groups include but are not limited to a furanyl, phenylene, thienyl, or pyrrolyl radical bonded two or more aryl groups.

When a named atom of an aromatic ring or a heterocyclic aromatic ring is defined as being "absent," the named atom is replaced by a direct bond. When the linking group or spacer group is defined as being absent, the linking group or spacer group is replaced by a direct bond.

"Alkylene" refers to a straight or branched bivalent aliphatic hydrocarbon group having from 1 to about 20 carbon atoms, e.g., 1, 2, 3, 4, 5, 6, 7, 8, 9, 10, 11, 12, 13, 14, 15, 16, 17, 18, 19, or 20 carbon atoms. The alkylene group can be straight, branched or cyclic. The alkylene group also can be optionally unsaturated and/or substituted with one or more "alkyl group substituents." There can be optionally inserted along the alkylene group one or more oxygen, sulfur or substituted or unsubstituted nitrogen atoms (also referred to herein as "alkylaminoalkyl"), wherein the nitrogen substituent is alkyl as previously described. Exemplary alkylene groups include methylene (—$CH_2$—); ethylene (—$CH_2$—$CH_2$—); propylene (—$(CH_2)_3$—); cyclohexylene (—$C_6H_{10}$—); —CH=CH—CH=CH—; —CH=CH—$CH_2$—; N(R)—$(CH_2)_r$—, wherein each of q and r is independently an integer from 0 to about 20, e.g., 0, 1, 2, 3, 4, 5, 6, 7, 8, 9, 10, 11, 12, 13, 14, 15, 16, 17, 18, 19, or 20, and R is hydrogen or lower alkyl; methylenedioxyl (—O—$CH_2$—O—); and ethylenedioxyl (—O—$(CH_2)_2$—). An alkylene group can have about 2 to about 3 carbon atoms and can further have 6-20 carbons.

As used herein, the term "acyl" refers to an organic acid group wherein the —OH of the carboxyl group has been replaced with another substituent (i.e., as represented by RCO—, wherein R is an alkyl or an aryl group as defined herein). As such, the term "acyl" specifically includes arylacyl groups, such as an acetylfuran and a phenacyl group. Specific examples of acyl groups include acetyl and benzoyl.

"Cyclic" and "cycloalkyl" refer to a non-aromatic mono- or multicyclic ring system of about 3 to about 10 carbon atoms, e.g., 3, 4, 5, 6, 7, 8, 9, or 10 carbon atoms. The cycloalkyl group can be optionally partially unsaturated. The cycloalkyl group also can be optionally substituted with an alkyl group substituent as defined herein. There can be optionally inserted along the cyclic alkyl chain one or more oxygen, sulfur or substituted or unsubstituted nitrogen atoms, wherein the nitrogen substituent is hydrogen, alkyl, substituted alkyl, aryl, or substituted aryl, thus providing a heterocyclic group. Representative monocyclic cycloalkyl rings include, but are not limited to, cyclopropyl, cyclobutyl, cyclopentyl, cyclohexyl, cycloheptyl, and the like. Further, the cycloalkyl group can be optionally substituted with a linking group, such as an alkylene group as defined hereinabove, for example, methylene, ethylene, propylene, and the like. In such cases, the cycloalkyl group can be referred to as, for example, cyclopropylmethyl, cyclobutylmethyl, and the like. Additionally, multicyclic cycloalkyl rings include adamantyl, octahydronaphthyl, decalin, camphor, camphane, and noradamantyl.

"Alkoxyl" or "alkoxyalkyl" refer to an alkyl-O—group wherein alkyl is as previously described. The term "alkoxyl" as used herein can refer to $C_{1-20}$ inclusive, linear, branched, or cyclic, saturated or unsaturated oxo-hydrocarbon chains, including, for example, methoxyl, ethoxyl, propoxyl, isopropoxyl, butoxyl, t-butoxyl, and pentoxyl.

"Aryloxyl" refers to an aryl-O—group wherein the aryl group is as previously described, including a substituted aryl. The term "aryloxyl" as used herein can refer to phenyloxyl or hexyloxyl, and alkyl, substituted alkyl, halo, or alkoxyl substituted phenyloxyl or hexyloxyl.

"Aralkyl" refers to an aryl-alkyl-group wherein aryl and alkyl are as previously described, and included substituted aryl and substituted alkyl. Exemplary aralkyl groups include benzyl, phenylethyl, and naphthylmethyl.

"Aralkyloxyl" refers to an aralkyl-O—group wherein the aralkyl group is as previously described. An exemplary aralkyloxyl group is benzyloxyl.

"Dialkylamino" refers to an —NRR' group wherein each of R and R' is independently an alkyl group and/or a substituted alkyl group as previously described. Exemplary alkylamino groups include ethylmethylamino, dimethylamino, and diethylamino.

"Alkoxycarbonyl" refers to an alkyl-O—CO—group. Exemplary alkoxycarbonyl groups include methoxycarbonyl, ethoxycarbonyl, butyloxycarbonyl, and t-butyloxycarbonyl.

"Aryloxycarbonyl" refers to an aryl-O—CO—group. Exemplary aryloxycarbonyl groups include phenoxy- and naphthoxy-carbonyl.

"Aralkoxycarbonyl" refers to an aralkyl-O—CO—group. An exemplary aralkoxycarbonyl group is benzyloxycarbonyl.

"Carbamoyl" refers to an $H_2N$—CO—group.

"Alkylcarbamoyl" refers to a R'RN—CO—group wherein one of R and R' is hydrogen and the other of R and R' is alkyl and/or substituted alkyl as previously described.

"Dialkylcarbamoyl" refers to a R'RN—CO—group wherein each of R and R' is independently alkyl and/or substituted alkyl as previously described.

"Acyloxyl" refers to an acyl-O—group wherein acyl is as previously described.

"Acylamino" refers to an acyl-NH—group wherein acyl is as previously described.

The term "alkenylene" denotes an acyclic carbon chain (i.e., having an open-chain structure) having a carbon-to-carbon double bond and is represented by the formula $C_nH_{2n-2}$, which optionally can be substituted one or more times. Representative alkenylene groups include, but are not limited to, ethenylene, propenylene, 1- or 2-butenylene, 1-, or 2-pentylene, and the like.

"Aroylamino" refers to an aroyl-NH—group wherein aroyl is as previously described.

The term "amino" refers to the —$NH_2$ group.

The term "carbonyl" refers to the —(C=O)—group.

The term "carboxyl" refers to the —COOH group.

The term "cyano" refers to the —CN group.

The terms "halo", "halide", or "halogen" as used herein refer to fluoro, chloro, bromo, and iodo groups.

The term "hydroxyl" refers to the —OH group.

The term "hydroxyalkyl" refers to an alkyl group substituted with an —OH group.

The term "mercapto" refers to the —SH group.

The term "oxo" refers to a compound described previously herein wherein a carbon atom is replaced by an oxygen atom.

The term "nitro" refers to the —$NO_2$ group.

The term "thio" refers to a compound described previously herein wherein a carbon or oxygen atom is replaced by a sulfur atom.

The term "sulfate" refers to the —$SO_4$ group.

The term "cycloalkenyl" refers to a partially unsaturated cyclic hydrocarbon group containing one or more rings, for example, one ring, two rings, three rings, or four rings, with three or more carbon atoms per ring, for example, 3, 4, 5, 6, 7, or 8 carbon atoms per ring. Exemplary cycloalkenyl groups include, but are not limited to, cyclopropenyl, cyclobutenyl, cyclopentenyl, cyclohexenyl, and the like.

The term "substituted cycloalkenyl" refers to a cycloalkenyl group substituted with one or more substituents, preferably 1, 2, 3, or 4 substituents, at any available point of attachment. Exemplary substituents include, but are not limited to, alkyl, substituted alkyl, halo, arylamino, acyl, hydroxyl, aryloxyl, alkoxyl, alkylthio, arylthio, aralkyloxyl, aralkylthio, carboxyl, alkoxycarbonyl, oxo, and cycloalkyl.

When the term "independently selected" is used, the substituents being referred to (e.g., R groups, such as groups $R_1$ and $R_2$, or groups X and Y), can be identical or different. For example, both $R_1$ and $R_2$ can be substituted alkyls, or $R_1$ can be hydrogen and $R_2$ can be a substituted alkyl, and the like.

A named "R", "R¹", "X", "Y", "Y'", "A", "A'", "B," "L," or "Z" group will generally have the structure that is recognized in the art as corresponding to a group having that name, unless specified otherwise herein. For the purposes of illustration, certain representative "R," "X," and "Y" groups as set forth above are defined below. These definitions are intended to supplement and illustrate, not preclude, the definitions that would be apparent to one of ordinary skill in the art upon review of the present disclosure.

The term "treatment" as used herein covers any treatment of a disease and/or condition in an animal or mammal, particularly a human, and includes: (i) preventing a disease, disorder and/or condition from occurring in a person which can be predisposed to the disease, disorder and/or condition, or at risk for being exposed to an agent that can cause the disease, disorder, and/or condition; but, has not yet been diagnosed as having it (ii) inhibiting the disease, disorder and/or condition, i.e., arresting its development; and (iii) relieving the disease, disorder and/or condition, i.e., causing regression of the disease, disorder and/or condition.

The term "mimetic" refers to a compound having similar functional and/or structural properties to another known compound or a particular fragment of that known compound, such as a known compound of biological origin, e.g., a polypeptide or fragment thereof.

"Binding specificity" refers to the ability of a protein or other type of molecule capable of recognizing and interacting with a complementary site on another protein or other type of molecule.

The term "pharmacophore", as used herein, refers to a specific model or representation of a molecular moiety capable of exerting a selected biochemical effect, e.g., inhibition of an enzyme, binding to a receptor, chelation of an ion, and the like. A selected pharmacophore can have more than one biochemical effect, e.g., can be an inhibitor of one enzyme and an agonist of a second enzyme. A therapeutic agent can include one or more pharmacophores, which can have the same or different biochemical activities.

The term "derivative" as used herein refers to a compound chemically modified so as to differentiate it from a parent compound. Such chemical modifications can include, for example, replacement of hydrogen by an alkyl, acyl, or amino group. A derivative compound can be modified by, for example, glycosylation, pegylation, or any similar process that retains at least one biological or immunological function of the compound from which it was derived.

The term "hydrophilicity" is used in the common manner of the field as having an affinity for water; readily absorbing and/or dissolving in water.

The term "lipophilicity" is used in the common manner of the field as having an affinity for, tending to combine with, or capable of dissolving in lipids.

The term "amphipathicity", as used herein, describes a structure having discrete hydrophobic and hydrophilic regions. Thus, one portion of the structure interacts favorably with aqueous and other polar media, while another portion of the structure interacts favorably with non-polar media.

The term "solubility" as used herein, describes the maximum amount of solute that will dissolve in a given amount of solvent at a specified temperature.

The term "bioavailability" as used herein refers to the systemic availability (i.e., blood/plasma levels) of a given amount of compound administered to a subject. The term further encompasses the rate and extent of absorption of compound that reaches the site of action.

II. COMPOUNDS

The presently disclosed subject matter provides compounds having binding specificity for a p75$^{NTR}$ receptor molecule. These compounds, along with related pharmaceutical compounds and methods, are useful in the treatment and prevention of neurodegenerative and other disorders.

The disclosed compounds are labeled herein as follows:

TABLE I

Structures of Compounds 1-6

| Compound | Name |
|---|---|
| 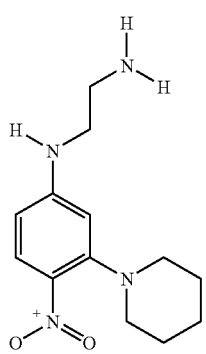 | Compound 1 (also referred to herein as "LM11A-28") |
| 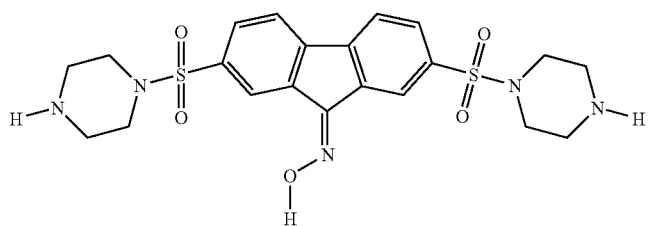 [SMILES: O=S(=O)(c1ccc2c(c1)C(=NO)c1cc(S(=O)(=O)N3CCNCC3)ccc1-2)N1CCNCC1] | Compound 2 (also referred to herein as "LM11A-7") |

TABLE I-continued

Structures of Compounds 1-6

| Compound | Name |
|---|---|
| [structure] | Compound 3 (also referred to herein as "LM11A-24", "24", and "C24") |
| [structure] | Compound 4 (also referred to herein as "LM11A-31" and "31") |
| [structure] | Compound 5 (also referred to herein as "LM11A-36", "36", and "C36") |
| [structure] | Compound 6 (also referred to herein as "LM11A-38" and "C38") |
| [structure] | Compound 7 |

II.A. Structure

In accordance with the presently disclosed subject matter, a representative compound or mimetic of a neurotrophin β-turn loop having binding specificity for a p75$^{NTR}$ receptor molecule comprises a compound selected from the group consisting of:

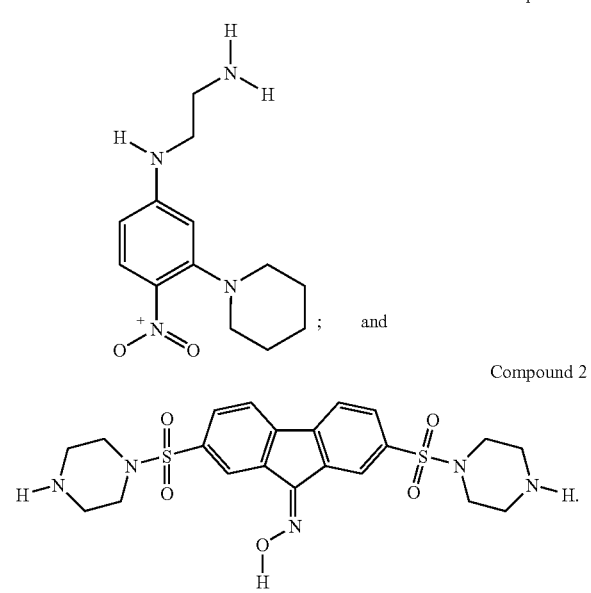

Compound 1

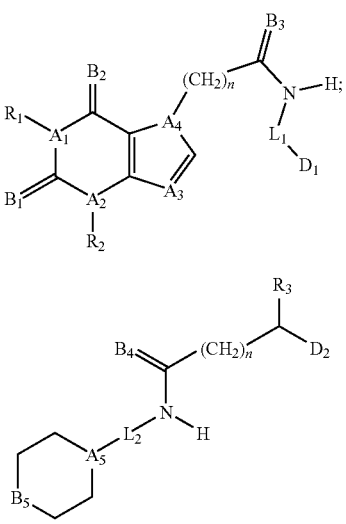

Compound 2

In some embodiments disclosed is a compound having a structure of Formula (I) or (II):

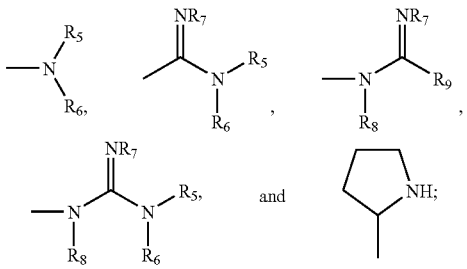

(I)

(II)

wherein, n is an integer from 0 to 8;

$L_1$ and $L_2$ are a linking group selected from the group consisting of alkylene, substituted alkylene, cycloalkyl, substituted cycloalkyl, cycloalkenyl, substituted cycloalkenyl, aryl, substituted aryl, alkenylene, and substituted alkenylene;

$R_1$, $R_2$, and $R_3$ are each independently selected from the group consisting of H, alkyl, substituted alkyl, cycloalkyl, halo, cyano, nitro, mercapto, hydroxyl, alkoxyl, aryl, aryloxyl, substituted aryl, and aralkyloxyl;

$A_1$, $A_2$, $A_3$, $A_4$, and $A_5$ are each independently selected from the group consisting of N and CH;

$B_1$, $B_2$, $B_3$, $B_4$, and $B_5$ are each independently selected from the group consisting of O, S, and $NR_4$, wherein $R_4$ is selected from the group consisting of H, alkyl, substituted alkyl, cycloalkyl, aryl, and substituted aryl; and $D_1$ and $D_2$ are selected from the group consisting of:

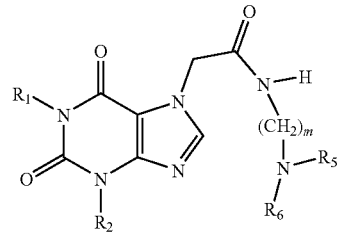

wherein, each $R_5$, $R_6$, $R_8$, $R_9$, and $R_{10}$ is independently selected from the group consisting of H, alkyl, substituted alkyl, cycloalkyl, aryl, substituted aryl, aralkyl, hydroxyalkyl, hydroxycycloalkyl, alkoxycycloalkyl, acyloxyl, alkylaminoalkyl, and alkoxycarbonyl; each $R_7$ is independently selected from the group consisting of H, hydroxyl, alkyl, substituted alkyl, aryl, substituted aryl, acyloxyl, and alkoxyl; or $R_7$ and $R_5$ or $R_7$ and $R_9$ together represent a $C_2$ to $C_{10}$ alkyl, $C_2$ to $C_{10}$ hydroxyalkyl, or $C_2$ to $C_{10}$ alkene.

A particular group of exemplary compounds of formula (I) or (II) are those wherein $L_1$ and $L_2$ are each independently —$(CH_2)_m$—, wherein m is an integer from 1 to 8.

A particular exemplary compound of formula (I) is:

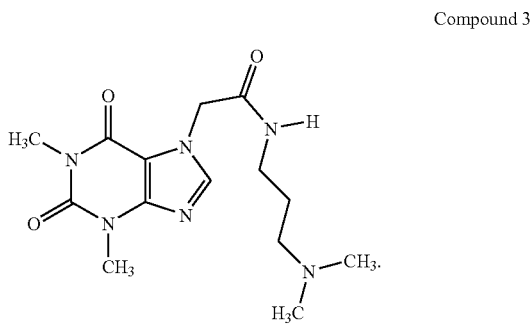

wherein, m is an integer from 1 to 8; $R_1$ and $R_2$ are each independently selected from the group consisting of H, alkyl, substituted alkyl, cycloalkyl, aryl, aryloxyl, substituted aryl, and aralkyloxyl; and $R_5$ and $R_6$ are each independently selected from the group consisting of H, alkyl, substituted alkyl, cycloalkyl, aryl, substituted aryl, aralkyl, hydroxyl, alkoxyl, hydroxyalkyl, hydroxycycloalkyl, alkoxycycloalkyl, aminoalkyl, acyloxyl, alkylaminoalkyl, and alkoxycarbonyl.

Another exemplary compound of formula (I) is:

Compound 3

A particular exemplary compound of Formula (II) has the following structure:

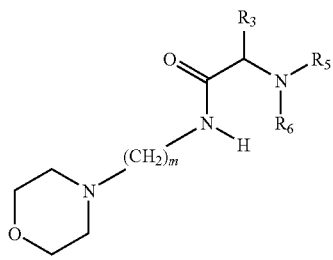

wherein m is an integer from 1 to 8; $R_3$ is selected from the group consisting of H, alkyl, substituted alkyl, cycloalkyl, halo, hydroxyl, alkoxyl, aryl, aryloxyl, substituted aryl, and aralkyloxyl; and $R_5$ and $R_6$ are each independently selected from the group consisting of H, alkyl, substituted alkyl, cycloalkyl, aryl, substituted aryl, aralkyl, hydroxyl, alkoxyl, hydroxyalkyl, hydroxycycloalkyl, alkoxycycloalkyl, aminoalkyl, acyloxyl, alkylaminoalkyl, and alkoxycarbonyl.

A further exemplary compound of Formula (II) has the following structure:

Compound 4

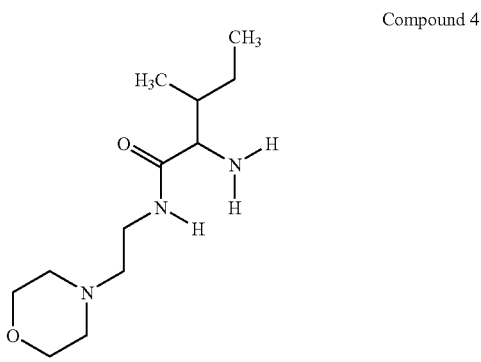

In some embodiments, a representative compound having binding specificity for a $p75^{NTR}$ receptor molecule has the formula:

Compound 7

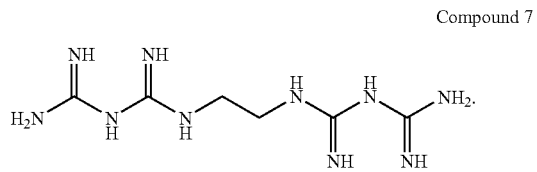 [SMILES: N=C(N)NC(=N)NCCNC(=N)NC(=N)N]

In accordance with the presently disclosed subject matter, a representative neurotrophin can include, but is not limited to, NGF. More particularly, the neurotrophin 8-turn loop having binding specificity for a $p75^{NTR}$ receptor molecule includes, but is not limited to, loop 1 of the NGF.

As disclosed herein, representative structures of the compound or mimetic having binding specificity for a $p75^{NTR}$ receptor molecule are capable of binding to the neurotrophin-binding site of the $p75^{NTR}$ receptor molecule.

The compounds disclosed herein can also encompass derivatives of a parent compound, which has binding specificity for a $p75^{NTR}$ receptor molecule, wherein the derivative also has binding specificity for the $p75^{NTR}$ receptor. The derivative can exhibit enhancement in at least one of the characteristics selected from the group consisting of hydrophilicity, lipophilicity, amphipathicity, solubility, bioavailability, and resistance to hepatic degradation, as compared to the parent compound.

It is to be understood that in some embodiments the compounds disclosed herein can encompass a pharmacophore substantially identical to the pharmacophore illustrated in FIG. 1c. Representative such compounds include but are not limited to compounds encompassed by Formulas (I) and (II).

II.B. Formulations

The compounds disclosed herein can be formulated in accordance with the routine procedures adapted for desired administration route. Accordingly, the compounds disclosed herein can take such forms as suspensions, solutions or emulsions in oily or aqueous vehicles, and can contain formulatory agents such as suspending, stabilizing and/or dispersing agents. The compounds disclosed herein can also be formulated as a preparation for implantation or injection. Thus, for example, the compounds can be formulated with suitable polymeric or hydrophobic materials (e.g., as an emulsion in an acceptable oil) or ion exchange resins, or as sparingly soluble derivatives (e.g., as a sparingly soluble salt). Alternatively, the active ingredient can be in powder form for constitution with a suitable vehicle, e.g., sterile pyrogen-free water, before use. Suitable formulations for each of these methods of administration can be found, for example, in *Remington: The Science and Practice of Pharmacy*, A. Gennaro, ed., 20th edition, Lippincott, Williams & Wilkins, Philadelphia, Pa.

For example, formulations for parenteral administration can contain as common excipients sterile water or saline, polyalkylene glycols such as polyethylene glycol, oils of vegetable origin, hydrogenated naphthalenes and the like. In particular, biocompatible, biodegradable lactide polymer, lactide/glycolide copolymer, or polyoxyethylene-polyoxypropylene copolymers can be useful excipients to control the release of active compounds. Other potentially useful parenteral delivery systems include ethylene-vinyl acetate copolymer particles, osmotic pumps, implantable infusion systems, and liposomes. Formulations for inhalation administration contain as excipients, for example, lactose, or can be aqueous solutions containing, for example, polyoxyethylene-9-auryl ether, glycocholate and deoxycholate, or oily solutions for administration in the form of nasal drops, or as a gel to be applied intranasally. Formulations for parenteral administration can also include glycocholate for buccal administration, methoxysalicylate for rectal administration, or citric acid for vaginal administration.

Further, formulations for intravenous administration can comprise solutions in sterile isotonic aqueous buffer. Where necessary, the formulations can also include a solubilizing agent and a local anesthetic to ease pain at the site of the injection. Generally, the ingredients are supplied either separately or mixed together in unit dosage form, for example, as a dry lyophilized powder or water free concentrate in a hermetically sealed container such as an ampule or sachet indicating the quantity of active agent. Where the compound is to be administered by infusion, it can be dispensed in a formulation with an infusion bottle containing sterile pharmaceutical grade water, saline or dextrose/water. Where the compound is administered by injection, an ampule of sterile water for injection or saline can be provided so that the ingredients can be mixed prior to administration.

Suitable formulations further include aqueous and non-aqueous sterile injection solutions that can contain antioxidants, buffers, bacteriostats, bactericidal antibiotics and solutes that render the formulation isotonic with the bodily fluids of the intended recipient; and aqueous and non-aqueous sterile suspensions, which can include suspending agents and thickening agents.

The compounds can further be formulated for topical administration. Suitable topical formulations include one or more compounds in the form of a liquid, lotion, cream or gel. Topical administration can be accomplished by application directly on the treatment area. For example, such application can be accomplished by rubbing the formulation (such as a lotion or gel) onto the skin of the treatment area, or by spray application of a liquid formulation onto the treatment area.

In some formulations, bioimplant materials can be coated with the compounds so as to improve interaction between cells and the implant.

Formulations of the compounds can contain minor amounts of wetting or emulsifying agents, or pH buffering agents. The formulations comprising the compound can be a liquid solution, suspension, emulsion, tablet, pill, capsule, sustained release formulation, or powder.

The compounds can be formulated as a suppository, with traditional binders and carriers such as triglycerides.

Oral formulations can include standard carriers such as pharmaceutical grades of mannitol, lactose, starch, magnesium stearate, polyvinyl pyrollidone, sodium saccharine, cellulose, magnesium carbonate, etc.

The pharmaceutical formulations comprising the compounds of the presently disclosed subject matter can include an agent which controls release of the compound, thereby providing a timed or sustained release compound.

II.C. Carriers

Pharmaceutically acceptable carriers are well known to those skilled in the art and include, but are not limited to, from about 0.01 to about 0.1 M and preferably 0.05M phosphate buffer or 0.8% saline. Such pharmaceutically acceptable carriers can be aqueous or non-aqueous solutions, suspensions and emulsions.

Examples of non-aqueous solvents suitable for use in the presently disclosed subject matter include, but are not limited to, propylene glycol, polyethylene glycol, vegetable oils such as olive oil, and injectable organic esters such as ethyl oleate.

Aqueous carriers suitable for use in the presently disclosed subject matter include, but are not limited to, water, ethanol, alcoholic/aqueous solutions, glycerol, emulsions or suspensions, including saline and buffered media. Oral carriers can be elixirs, syrups, capsules, tablets and the like.

Liquid carriers suitable for use in the presently disclosed subject matter can be used in preparing solutions, suspensions, emulsions, syrups, elixirs and pressurized compounds. The active ingredient can be dissolved or suspended in a pharmaceutically acceptable liquid carrier such as water, an organic solvent, a mixture of both or pharmaceutically acceptable oils or fats. The liquid carrier can contain other suitable pharmaceutical additives such as solubilizers, emulsifiers, buffers, preservatives, sweeteners, flavoring agents, suspending agents, thickening agents, colors, viscosity regulators, stabilizers or osmo-regulators.

Liquid carriers suitable for use in the presently disclosed subject matter include, but are not limited to, water (partially containing additives as above, e.g. cellulose derivatives, preferably sodium carboxymethyl cellulose solution), alcohols (including monohydric alcohols and polyhydric alcohols, e.g. glycols) and their derivatives, and oils (e.g. fractionated coconut oil and arachis oil). For parenteral administration, the carrier can also include an oily ester such as ethyl oleate and isopropyl myristate. Sterile liquid carriers are useful in sterile liquid form comprising compounds for parenteral administration. The liquid carrier for pressurized compounds disclosed herein can be halogenated hydrocarbon or other pharmaceutically acceptable propellant.

Solid carriers suitable for use in the presently disclosed subject matter include, but are not limited to, inert substances such as lactose, starch, glucose, methyl-cellulose, magnesium stearate, dicalcium phosphate, mannitol and the like. A solid carrier can further include one or more substances acting as flavoring agents, lubricants, solubilizers, suspending agents, fillers, glidants, compression aids, binders or tablet-disintegrating agents; it can also be an encapsulating material. In powders, the carrier can be a finely divided solid which is in admixture with the finely divided active compound. In tablets, the active compound is mixed with a carrier having the necessary compression properties in suitable proportions and compacted in the shape and size desired. The powders and tablets preferably contain up to 99% of the active compound. Suitable solid carriers include, for example, calcium phosphate, magnesium stearate, talc, sugars, lactose, dextrin, starch, gelatin, cellulose, polyvinylpyrrolidine, low melting waxes and ion exchange resins.

Parenteral carriers suitable for use in the presently disclosed subject matter include, but are not limited to, sodium chloride solution. Ringer's dextrose, dextrose and sodium chloride, lactated Ringer's and fixed oils. Intravenous carriers include fluid and nutrient replenishers, electrolyte replenishers such as those based on Ringer's dextrose and the like. Preservatives and other additives can also be present, such as, for example, antimicrobials, antioxidants, chelating agents, inert gases and the like.

Carriers suitable for use in the presently disclosed subject matter can be mixed as needed with disintegrants, diluents, granulating agents, lubricants, binders and the like using conventional techniques known in the art. The carriers can also be sterilized using methods that do not deleteriously react with the compounds, as is generally known in the art.

II.D. Salts

It is also to be understood that the disclosed compounds can further comprise pharmaceutically acceptable salts.

Such salts include, but are not limited to, pharmaceutically acceptable acid addition salts, pharmaceutically acceptable base addition salts, pharmaceutically acceptable metal salts, ammonium and alkylated ammonium salts.

Acid addition salts include salts of inorganic acids as well as organic acids. Representative examples of suitable inorganic acids include hydrochloric, hydrobromic, hydroiodic, phosphoric, sulfuric, nitric acids and the like. Representative examples of suitable organic acids include formic, acetic, trichloroacetic, trifluoroacetic, propionic, benzoic, cinnamic, citric, fumaric, glycolic, lactic, maleic, malic, malonic, mandelic, oxalic, picric, pyruvic, salicylic, succinic, methanesulfonic, ethanesulfonic, tartaric, ascorbic, pamoic, bismethylene salicylic, ethanedisulfonic, gluconic, citraconic, aspartic, stearic, palmitic, EDTA, glycolic, p-aminobenzoic, glutamic, benzenesulfonic, p-toluenesulfonic acids, sulphates, nitrates, phosphates, perchlorates, borates, acetates, benzoates, hydroxynaphthoates, glycerophosphates, ketoglutarates and the like.

Base addition salts include but are not limited to, ethylenediamine. N-methyl-glucamine, lysine, arginine, ornithine, choline, N,N'-dibenzylethylenediamine, chloroprocaine, diethanolamine, procaine. N-benzylphenethylamine, diethylamine, piperazine, tris(hydroxymethyl)-aminomethane, tetramethylammonium hydroxide, triethylamine, dibenzylamine, ephenamine, dehydroabietylamine. N-ethylpiperidine, benzylamine, tetramethylammonium, tetraethylammonium, methylamine, dimethylamine, trimethylamine, ethylamine, basic amino acids, e.g., lysine and arginine dicyclohexylamine and the like.

Examples of metal salts include lithium, sodium, potassium, magnesium salts and the like.

Examples of ammonium and alkylated ammonium salts include ammonium, methylammonium, dimethylammonium, trimethylammonium, ethylammonium, hydroxyethylammonium, diethylammonium, butylammonium, tetramethylammonium salts and the like. Examples of organic bases include lysine, arginine, guanidine, diethanolamine, choline and the like.

III. METHODS OF USE

The presently disclosed subject matter provides novel methods of treating neurodegenerative and other disorders or conditions in a subject. More particularly, the methods of the presently disclosed subject matter involve the administration of a compound having binding specificity for a $p75^{NTR}$ receptor molecule in a subject to treat a neurodegenerative disorder or other disorder or condition. The compound can be administered in an amount effective to induce survival signaling and/or inhibit proNGF-induced cell death, which has been determined to be associated with neurodegenerative and other disorders.

The condition to be treated can be any condition which is mediated, at least in part, by binding of neurotrophins to the $p75^{NTR}$ receptor. Such conditions include, but are not limited to, Alzheimer's disease, Huntington's disease, Pick's disease, amyotrophic lateral sclerosis, epilepsy, Parkinson's disease, spinal cord injury, stroke, hypoxia, ischemia, brain injury, diabetic neuropathy, peripheral neuropathy, nerve transplantation, multiple sclerosis, peripheral nerve injury, hair loss, conditions involving degeneration or dysfunction of cells expressing p75.

The compounds having binding specificity for a $p75^{NTR}$ receptor molecule can be used to treat neural degeneration, including preventing neurodegeneration such as, for example, neurodegeneration caused by chemotherapy and/or neurodegerative disorders, as well as other conditions such as inducing hair follicle cell survival caused by, for example, chemotherapy.

The presently disclosed subject matter further provides for novel methods of facilitating cell survival. Representative cells include, but are not limited to, septal, hippocampal, cortical, sensory, sympathetic, motor neurons, hair follicle cells, progenitor, and stem cells. Specifically, the methods comprise treating a cell with a compound having binding specificity for a $p75^{NTR}$ receptor molecule, whereby the compound induces survival signaling and inhibits proNGF-induced cell death.

III.A. Administration

The presently disclosed subject matter discloses a method of administering compounds having binding specificity for a $p75^{NTR}$ receptor compound in order to ameliorate a condition mediated by $p75^{NTR}$ binding in a subject. The method can comprise the step of administering to a subject an effective amount of a compound having binding specificity for a $p75^{NTR}$ receptor, such as any of the compounds disclosed herein.

As used herein, administering can be effected or performed using any of the various methods known to those skilled in the art. The compound can be administered, for example, subcutaneously, intravenously, parenterally, intraperitoneally, intradermally, intramuscularly, topically, enteral (e.g., orally), rectally, nasally, buccally, sublingually, vaginally, by inhalation spray, by drug pump or via an implanted reservoir in dosage formulations containing conventional non-toxic, physiologically acceptable carriers or vehicles.

Further, the presently disclosed compounds can be administered to a localized area in need of treatment. This can be achieved by, for example, and not by way of limitation, local infusion during surgery, topical application, transdermal patches, by injection, by catheter, by suppository, or by implant (the implant can optionally be of a porous, non-porous, or gelatinous material), including membranes, such as sialastic membranes or fibers.

The form in which the compound is administered (e.g., syrup, elixir, capsule, tablet, solution, foams, emulsion, gel, sol) will depend in part on the route by which it is administered. For example, for mucosal (e.g., oral mucosa, rectal, intestinal mucosa, bronchial mucosa) administration, nose drops, aerosols, inhalants, nebulizers, eye drops or suppositories can be used. The compound can also be used to coat bioimplantable materials to enhance neurite outgrowth, neural survival, or cellular interaction with the implant surface. The compounds and agents disclosed herein can be administered together with other biologically active agents, such as analgesics, anti-inflammatory agents, anesthetics and other agents which can control one or more symptoms or causes of a $p75^{NTR}$-mediated condition.

Additionally, administration can comprise administering to the subject a plurality of dosages over a suitable period of time. Such administration regimens can be determined according to routine methods, upon a review of the instant disclosure.

The compounds of the presently disclosed subject matter can be employed as the sole active agent in a pharmaceutical or can be used in combination (e.g., administered proximate in time to each other or even in the same formulation) with other active ingredients, e.g., neurotrophins, or other factors or drugs which can facilitate neural survival or axonal growth in neurodegenerative diseases, including but not limited to amyloid-β inhibitors, acetylcholinesterase inhibitors, butyrylcholinesterase inhibitors, and N-methyl-D-aspartate subtype of glutamate receptor antagonists.

III.B. Dosage

For administration of a compound as disclosed herein, conventional methods of extrapolating human dosage based on doses administered to a murine animal models can be carried out using the conversion factor for converting the mouse dosage to human dosage: Dose Human per kg=Dose Mouse per kg×12 (Freireich et al., (1966) *Cancer Chemother Rep.* 50, 219-244\. Drug doses can also be given in milligrams per square meter of body surface area rather than body weight, as this method achieves a good correlation to certain metabolic and excretionary functions. Moreover, body surface area can be used as a common denominator for drug dosage in adults and children as well as in different animal species (Freireich et al., (1966) *Cancer Chemother Rep.* 50, 219-244). Briefly, to express a mg/kg dose in any given species as the equivalent mg/sq m dose, the dosage is multiplied by the appropriate km factor. In an adult human, 100 mg/kg is equivalent to 100 mg/kg×37 kg/sq m=3700 mg/m².

Insofar as the compounds disclosed herein can take the form of a mimetic or fragment thereof, it is to be appreciated that the potency, and therefore dosage of an effective amount can vary. However, one skilled in the art can readily assess the potency of a compound of the type presently envisioned by the presently disclosed subject matter.

The compounds disclosed herein can be used in unit dosage form and can be prepared by any of the methods well known in the pharmaceutical art, or example, as described in *Remington's Pharmaceutical Sciences* (Mack Pub. Co., Easton, Pa., 1980).

Representative dosages of the presently disclosed compounds are 10 to 100 μg/gram body weight for a murine model. It will be appreciated by one of skill in the art that dosage range will depend on the particular compound, and its potency. The dosage range is understood to be large enough to produce the desired effect in which the neurodegenerative or other disorder and the symptoms associated therewith are ameliorated and/or survival of the cells is achieved, but not be so large as to cause unmanageable adverse side effects. The appropriate range for therapeutic effectiveness will be readily determined by one skilled in the art depending on the route of administration, age, and condition of the subject being treated. The dosage can also be adjusted by the individual physician in the event of any complication. No unacceptable toxicological effects are expected when compounds disclosed herein are used in accordance with the presently disclosed subject matter.

An effective amount of the compounds disclosed herein comprise amounts sufficient to produce a measurable biological response. Actual dosage levels of active ingredients in a therapeutic compound of the presently disclosed subject matter can be varied no as to administer an amount of the active compound that is effective to achieve the desired therapeutic response for a particular subject and/or application. Preferably, a minimal dose is administered, and the dose is escalated in the absence of dose-limiting toxicity to a minimally effective amount. Determination and adjustment of a therapeutically effective dose, as well as evaluation of when and how to make such adjustments, are known to those of ordinary skill in the art.

Further with respect to the methods of the presently disclosed subject matter, a preferred subject is a vertebrate subject. A preferred vertebrate is warm-blooded; a preferred warm-blooded vertebrate is a mammal. The subject treated by the presently disclosed methods is desirably a human, although it is to be understood that the principles of the presently disclosed subject matter indicate effectiveness with respect to all vertebrate species which are to be included in the term "subject." In this context, a vertebrate is understood to be any vertebrate species in which treatment of a neurodegenerative disorder is desirable. As used herein, the term "subject" includes both human and animal subjects. Thus, veterinary therapeutic uses are provided in accordance with the presently disclosed subject matter.

As such, the presently disclosed subject matter provides for the treatment of mammals such as humans, as well as those mammals of importance due to being endangered, such as Siberian tigers; of economic importance, such as animals raised on farms for consumption by humans; and/or animals of social importance to humans, such as animals kept as pets or in zoos. Examples of such animals include but are not limited to: carnivores such as cats and dogs; swine, including pigs, hogs, and wild boars; ruminants and/or ungulates such as cattle, oxen, sheep, giraffes, deer, goats, bison, and camels; and horses. Also provided is the treatment of birds, including the treatment of those kinds of birds that are endangered and/or kept in zoos, as well as fowl, and more particularly domesticated fowl, i.e., poultry, such as turkeys, chickens, ducks, geese, guinea fowl, and the like, as they are also of economical importance to humans. Thus, also provided is the treatment of livestock, including, but not limited to, domesticated swine, ruminants, ungulates, horses (including race horses), poultry, and the like.

EXAMPLES

The following Examples have been included to provide illustrations of the presently disclosed subject matter. In light of the present disclosure and the general level of skill in the art, those of skill will appreciate that the following Examples are intended to be exemplary only and that numerous changes, modifications and alterations can be employed without departing from the spirit and scope of the presently disclosed subject matter.

Materials and Methods for Examples

Computational Studies

Computational studies were performed using the Accelrys Catalyst® and InsightII systems obtained from Accelerys (San Diego, Calif., United States of America).

Antibodies and Proteins

Polyclonal rabbit anti-NOF antibody was obtained from Chemicon (Temecula, Calif., United States of America). Monoclonal anti-phospho-ERK$^{T202/Y204}$, polyclonal anti-ERK42/44, monoclonal anti-phospho-A-T$^{S473}$, polyclonal anti-AKT, polyclonal anti-phospho-NFκB-p65(Ser$^{563}$), and site-specific polyclonal anti-Trk$^{Y490}$ were obtained from Cell Signaling Technology, Inc. (Beverly, Mass., United States of America). Monoclonal anti-NFκB-p65 was obtained from Santa Cruz Biotechnology, Inc. (Santa Cruz, Calif., United States of America). Monoclonal anti-actin was obtained from Sigma-Aldrich Corp. (St. Louis, Mo., United States of America). Polyclonal TrkA and TrkB antibodies were obtained from Upstate USA, Inc. (Charlottesville, Va., United States of America). Anti-pan-Trk 1087 and 1088 were previously characterized (Zhou, Holtzman, D. M., Weiner, R. I., Mobley, W. C. (1994) *Proc Natl Acad Sci USA* 91, 3824) and obtained from Dr. William C. Mobley (Stanford University, California, United States of America). p75$^{NTR}$ polyclonal rabbit antibodies 9651 (Huber, L. J., Chao, M. V. (1995) *Dev Bio* 167, 227-238) and 9650 raised against the neurotrophin-binding region (residues 43-161, cysteine repeat regions II, III, and IV) of the extracellular domain of recombinant p75 were provided by Dr. Moses Chao (Skirball Inst., NYU, New York, United States of America). Recombinant human NGF was obtained from Invitrogen (Carlsbad, Calif., United States of America) and BDNF from Sigma-Aldrich (St. Louis, Mo., United States of America). P75$^{NTR}$/Fc and TrkA/Fc chimerae were obtained from R&D Systems (Minneapolis, Minn., United States of America). Furin resistant pro-NGF was prepared as previously described (Beattie, M. S. et al., (2002) *Neuron* 36, 375-386).

Neural Bioassays

Hippocampal neurons were prepared from E16-17 mouse embryos as previously described (Yang, T. et al. (2003) *J Neurosci* 23, 3353-3363). Low density cultures were initiated in poly-L-lysine coated N2 plates by adding 25 μl of cell suspension (2000 neurons/well; 12,500 cells/cm$^2$), 25 μl of DMEM containing 10% FBS, and different concentrations of recombinant BDNF, NGF, or p75-binding compounds to each well. For studies employing p75$^{NTR+/+}$ and p75$^{NTR-/-}$ neurons, mice carrying a mutation in exon 3 of the p75$^{NTR}$ gene (Lee. K. F. et al. (1992) *Cell* 69, 737-749) were bred onto a B6 congenic background (>10 B6 backcrosses).

After 48 hours in culture, cell survival was assessed as previously described (Longo, F. M., Manthorpe, M., Xie, Y. M., Varon, S. (1997) *J Neurosci Res* 48, 1-17) using a combination of standard morphological criteria along with visual determination of whether a given cell converted MTT to its blue formazan product. The number of surviving neurons was determined by counting the total number of cells in each well that were both morphologically intact and filed with blue product (Longo F. M., Manthorpe, M., Xie, Y. M., Varon, S. (1997) *J Neurosci Res* 48, 1-17). For each neurotrophin or compound concentration, duplicate wells were counted and the resulting values averaged. Activity of each compound was confirmed by blinded counts. Counts were normalized to survival achieved with 25 ng/ml BDNF or to baseline survival. Fitting of dose-responsive curves was performed with Sigmaplot obtained from SYSTAT Software Inc. (Richmond, Calif., United States of America).

For signaling pathway inhibitor studies, LY294002, PD98059 (obtained from EMD Biosciences/Calbiochem, San Diego, Calif., United States of America), and SN50 (obtained from Alexis Corp., Lausen, Switzerland) were added to cultures at final concentrations of 25 µM, 50 µM, and 2.5 µg/ml respectively, concomitantly with BDNF, NGF, or p75-binding compounds. For antibody inhibition studies, $p75^{NTR}$ antisera and control non-immune serum were used at a final dilution of 1:100 in the presence of BDNF, NGF, or p75-binding compounds. For all studies applying signaling inhibitors, $p75^{NTR}$ antibodies or $p75^{NTR-/-}$ neurons, survival was assessed at 48 hours.

Protein Extraction and Western Blot Analysis

For assays of Trk, AKT, NFκB, and ERK activation, hippocampal neurons derived from E16-17 mice were cultured in poly-L-lysine coated six-well plates (Corning, Inc., Corning, N. Y, United States of America) in DMEM containing 10% FBS, followed by incubation in serum-free DMEM for 2 hours before addition of neurotrophins or compounds. At the indicated time points, neurons were harvested in lysis buffer consisting of: 20 mM Tris, pH 8.0, 137 mM NaCl, 1% Igepal CA-630, 10% glycerol, 1 mM PMSF, 10 µg/ml aprotinin, 1 µg/ml leupeptin, 500 µM orthovanadate (Zhou, J., Valletta, J. S., Grimes, M. L., Mobley, W. C. (1995) *J Neurochem* 65, 1146-1156).

Lysates were centrifuged, the supernatant collected, and protein concentrations determined using the BCA Protein Assay Reagent obtained from Pierce (Rockford, Ill., United States of America). Western blots were performed as described previously (Yang. T. et al. (2003) *J Neurosci* 23, 3353-3363). Western blot signals were detected using the ECL Chemiluminescence System obtained by Amersham (Piscataway, N. J, United States of America) (Yang, T. et al. (2003) *J Neurosci* 23, 3353-3363).

NGF Displacement from $p75^{NTR}$ and TrkA

NGF ELISA was performed as previously described (Longo. F. M. at at (1999) *J Neurosci Res* 55, 230-237). Briefly, 96-well plates were incubated with 0.1 pmol (at 1 nM) of p75/Fc or TrkA/Fc recombinant protein obtained from R&D System (Minneapolis, Minn., United States of America) overnight at 4° C. followed by incubation with blocking buffer for 1 hour at room temperature. ProNGF at 100 ng/ml or different concentrations of NGF, and p75-binding compounds were diluted in sample buffer, added to the wells, and incubated for 6 hours with shaking at room temperature. Plates were than washed five times with Tris-buffered saline (TBS) containing 0.05% Tween-20 and incubated with anti-NGF rabbit polyclonal antibody overnight at 4° C. Following five washes with TBS, wells were incubated for 2.5 hours at room temperature with anti-rabbit IgG HRP conjugate and washed five times. 3,3',5,5'-tetramethyl-benzidine substrate was added and the optical density measured at 450 nm.

$p75^{NTR}$ Antibody Competition

NIH3T3 fibroblasts expressing either null vector or $p75^{NTR}$ (Huang, C. S. et al. (1999) *J Biol Chem* 274, 36707-36714) were obtained from Dr. William Mobley (Stanford University, California, United States of America). Cells were grown in monolayers, harvested in PBS with 2 mM EDTA, pelleted, and resuspended in ice-cold DMEM HEPES with 1 mg/ml BSA. $6-9 \times 10^6$ cells from one confluent 6-well plate were used for each experimental point.

For binding analysis, $p75^{NTR}$ antibody (1:100) was allowed to bind in the presence or absence of 100 nM p75-binding compounds for 90 minutes at 4° C. with gentle rotation, followed by four washes in PBS. The final cell pellet was resuspended in lysis buffer.

Western blots were performed as described above. To detect the presence of $p75^{NTR}$ antibody, blots were probed with horseradish peroxidase-linked goat anti-rabbit IgG obtained from Amersham/Pharmacia Biotech (Piscataway, N. J, United States of America). Signals were detected by the ECL chemiluminescence system obtained from Amersham Biosciences (Piscataway, N. J, United States of America). To control for variation in protein loading, the blot was stripped and reprobed with β-actin monoclonal antibody obtained from Sigma (St. Louis, Mo., United States of America).

Olipodendrocyte Culture, Pro-Neurotrophin Treatment and Cell Death Assay

Cortical oligondendrocytes from rat pups were prepared as previously described (Yoon et al. (1998) *J Neurosci* 18, 3273-3281, Harrington, A. W., Kim, J. Y., Yoon, S. O. (2002) *J Neurosci* 22, 156-166). Cells were treated with recombinant, cleavage-resistant proNGF at 0.05 nM (2.8 ng/ml). Controls were treated with equivalent volumes of proNGF purification buffer containing 350 mM imidazole. 24 hours after treatment, the cells were fixed and processed for MBP and TUNEL staining as previously described (Beattie, M. S. et al. (2002) *Neuron* 36, 375-386). 200-250 cells were counted per well, for a minimum of 600 cells per experimental condition.

Example 1

Computational Modeling, Pharmacophore Generation, Virtual and Functional Screening In order to generate a productive pharmacophore emulating a loop structure likely to interact with a receptor, it was hypothesized that (1) the degrees of freedom of the ligand peptide structure are restricted by its residence in the protein, and (2) there is little "induced fit" involving changes in loop structure at the targeted receptor subsite, or it is accommodated by flexibility of the small molecule ligand. When both of these conditions apply, they allow an interacting/activating small molecule conformation that interacts with the receptor in a manner similar to that of the native ligand.

Computational studies of active dimeric cyclic peptides mimicking NGF β-hairpin loops suggest that energetic and structural constraints would disallow simultaneous β-hairpin folding of both peptide subunits, implying that the peptides act in a monomeric fashion. Additionally, based on early virtual screening of 3D conformer libraries, the presence of many functionally dimeric non-peptide molecules having a molecular weight of less than 500D was unlikely.

Therefore, efforts were focused on locating compounds emulating a single loop 1 structure. Compounds were selected for screening in cell survival assays using the protocol outlined in FIG. 1. Computational studies suggested that in situ, the tethered loop 1 backbone and proximal portions of the side chain structure had restricted degrees of freedom, and an intermediate structure chosen from an ensemble of samples from loop molecular dynamics simulations was extracted and used to build a novel pharmocophoric model (FIG. 1a). Guidance for the placement of pharmacophore features was obtained from consideration of loop phylogeny, side chain chemistry, and the inventors' experience with synthetic active peptides.

As a first approximation, it was assumed that analogous loop 1 domains from neurotrophins of different species and different neurotrophin family members should bind similarly to $p75^{NTR}$. The primary structure of BDNF loop 1 diverged significantly from NGF and NT-3, and in efforts to reduce pharmacophore complexity, only the latter two were utilized. The propensity of histidine to act as a hydrogen bond donor (McDonald. I, Thornton, J. M., (1994) *WWW Edition December* 1994) suggested its use at position 34, while the K to R transition at position 32 suggested the Use of a positively ionizable feature at that location (FIGS. 1*b* and 1*c*).

An average of 35 conformers of each of over 800,000 compounds were screened against the novel pharmacophore, yielding approximately 800 that fit with a calculated internal energy of less than 10 kcal/mol (FIG. 1*d*). This number was reduced to approximately 60 by visual inspection on the basis of likely steric compatibility with a hypothetical shallow receptor binding pocket, and maximal flexibility of the functional groups. 35 compounds were obtained initially, of which 23 were soluble in water.

In preliminary studies using a chicken DRG neuronal survival assay, 4 of 23 compounds tested showed significant activity. Further analysis was carried out using embryonic mouse hippocampal neurons. Under conditions of low density and lack of glial support, the survival of these neurons was dependent, in part, on the addition of neurotrophins to the cultures.

Screening of 23 previously tested compounds in these hippocampal cultures demonstrated activity of three of the compounds (Compounds 2-4) identified as having activity using DRG cultures, and also identified fourth and fifth active compounds (Compounds 1 and 7) through DRG and hippocampal assays. The results corresponded to a 17% yield for the screening procedure. In further support for this method, in preliminary studies based on models of NGF loop 4 (LM14A), a high positive rate of identification of active compounds was achieved (3 positive of 8 compounds screened (37%)).

A regression analysis of NGF-$p75^{NTR}$ binding in the presence of the p75-binding compounds was performed. The data was fit using the Nonlinear Regression module of Sigmaplot, to a modification of the Gaddum/Schild equation (adapted from Motulskv. H. J., and Christopoulos, A. (2003) *A Practical Guide to Curve Fitting,* $2^{nd}$ edn. (San Diego, Calif., GraphPad Software, Inc.):

$$\text{Signal} = \frac{\text{top} - \text{bottom}}{1 + \left( \frac{10^{logEC50}\left[1 + \left(\frac{[C]}{10^{logA_2}}\right)\right]^S}{[NGF]} \right)^{HillSlope}} + \text{bottom}$$

where, top=maximal signal; bottom=basal signal; [C]=compound concentration; S=Schild coefficient; HillSlope=Hill coefficient; [NGF]=NGF concentration, $EC_{50}$=concentration of NGF resulting in 50% maximal (top-bottom) binding; and $A_2$=concentration of compound resulting in a doubling of the $EC_{50}$ from the unshifted curve. Herein, the calculated Hill slope ranged from 1.0 to 1.6 and was generally not significantly different from 1.

Example 2

Compounds Promote Hippocampal Neuron Survival

High-throughput virtual screening based on neurotrophin loop 1 models and small-scale in vitro bioassays were used to identify chemically diverse compounds with potent neurotrophic activity (FIG. 1). Approximately 800,000 compounds were screened in silico to produce a high yield of 4 positives out of 23 compounds submitted to in vitro screening (17%).

In order to understand the mechanisms of action of the selected compounds and test the conjecture that they work via the targeted receptor, $p75^{NTR}$, the dose-dependent relationships of the survival-promoting activities of the p75-binding compounds compared to NGF and BDNF using embryonic hippocampal neurons in culture conditions in which NGF promotes neural survival were examined. In the cultures, neurotrophic activity was mediated by BDNF principally through TrkB and $p75^{NTR}$, and by NGF primarily through $p75^{14m}$, as they express little TrkA (Brann, A. B., et al. (1999) *J Neurosci* 19, 8199-8206; Bui, N. T., et al. (2002) *J Neurochem* 81, 594-606).

Addition of Compounds 1-4 (FIG. 2*a*, structures) increased the number of GAP-43 positive neurite-bearing cells, consistent with increased neuronal survival (FIG. 2*a*, photomicrographs). Dose-response profiles of the active compounds (FIG. 2*b*) demonstrated $EC_{50}$ values in the range of 100-300 pM and intrinsic activities 80-100% of the NGF response. Independently synthesized preparations of Compounds 3 and 4 showed similar results. Compound 5, a compound structurally similar to Compound 3, showed little or no neurotrophic activity. The structures of Compounds 1-5 are illustrated in Table I.

For each compound, at concentrations greater than 5 nM, survival was reduced to baseline or below (FIG. 2*b*) as a result of mechanisms unrelated to $p75^{NTR}$, or from modulation of receptor multimer formation and survival signaling at higher receptor occupancies, even by a compound without neurotrophic activity (e.g., Compound 5). Response curves similar to that of NGF in the hippocampal neuron system are consistent with activation of survival signaling through the NGF binding region of $p75^{NTR}$.

Of the four compounds initially identified, the two (Compound 3, a derivative of caffeine, and Compound 4, an amino acid derivative) were predicted to have the most "drug-like" character by the Lipinski criteria (Lipinski, C. A (2000) *J Pharm Toxicol Methods* 44, 235-249) and blood-brain barrier calculations (Fu, X. C., Chen, C. X., Liana, W. Q., Yu, Q. S. (2001) *Acta Pharmacol Sin* 22, 663-668; Clark, D. E. (2002) *J Pharm Sci* 88, 815-821) were selected for more detailed mechanistic study. Compound 4 was prioritized, as preliminary studies indicated that it exhibits significant oral uptake and blood-brain barrier penetration. The relatively inactive Compound 5 was chosen as a negative control due to its structural similarity to Compound 3 (FIG. 2*a*).

Example 3

Compounds Interact With and Work Through $p75^{NTR}$ Receptors, Not Trk Receptors In order to assess the interactions of the p75-binding compounds with neurotrophin receptors, the effects of increasing concentrations of compounds on NGF binding to the recombinant chimeric proteins p75$^{NTR}$-Fc and TrkA-Fc were examined. In these experiments. Compound 4 (FIG. 3a) and Compound 3 (FIG. 3b), but not Compound 5 (FIG. 3c), shifted the NGF/p75$^{NTR}$-Fc biding curve significantly to the right. The inhibition of NGF binding caused by each active compound was reversed with increasing NGF concentration, consistent with a mechanism that is, at least in part, competitive in nature. When the data was fit to the Gaddum-Schild equation that describes ligand binding in the presence of an inhibitor (Motulskv. H. J., and Christopoulos, A. (2003) *A Practical Guide to Curve Fitting*, 2$^{nd}$ edn. (San Diego, Calif., GraphPad Software, Inc.)), the resulting Schild coefficients were significantly less than 1.0 for both active compounds (Compound 4, 0.58+/−0.04; Compound 3, 0.26+/−0.01), suggesting a more complex model, e.g., multiple ligand-receptor binding sites (Lutz. M., and Kenakin, T. (1999) *Quantitative Molecular Pharmacology and Informatics in Drug Discovery* (Hoboken, N. J: John Wiley & Sons); Neubig, R. R., Spedding, M, Kenakin, T., and Christopoulos, A. (2003) *Pharmacol Rev* 55, 597-606).

The results are consistent with models in which the effects of the compounds are due either to interaction with only a portion of the NGF binding surface of the receptor, and/or to allosteric effects indirectly affecting NGF binding. Gaddum-Schild analysis also yields a measure of potency known as $A_2$ (i.e., the concentration of compound that shifts the $EC_{50}$ twofold to the right) that can be equated with compound $K_D$ when the Schild coefficient is 1. The $A_2$ values derived for Compounds 4 and 3 were 1192+/−1.2 and 31.6+/−1.3 nM, respectively. However, since the Schild coefficients are significantly different from 1, the true $K_D$ values are unable to be determined.

In the case of Compound 4, the $EC_{50}$ value for its biologic effect is approximately 150 pM, while its $A_2$ is nearly four orders of magnitude greater. Large differences between biologic potency of small molecules and binding estimated by ligand displacement are common (Lutz. M., and Kenakin, T. (1999) *Quantitative Molecular Pharmacology and Informatics in Drug Discovery* (Hoboken, N. J: John Wiley & Sons)), and may have several causes, including: differences between receptor states in binding versus functional assays; post-receptor signal amplification, such that maximal biologic effects are seen at very low receptor occupancies; partial displacement of a multivalent ligand by a smaller antagonist; and that the compound works through a mechanism independent of the targeted receptor. The latter possibility was addressed using p75$^{NTR}$ blocking antibody and p75$^{NTR-/-}$ neurons to assess p75$^{NTR}$ dependence. Additionally, the specificity of p75-binding compounds for p75$^{NTR}$ is supported by the finding that the active compounds have no effect on NGF binding to TrkA (FIGS. 3d, 3e).

It was then determined that p75-binding compound activity is p75$^{NTR}$-dependent. Ab 9651, previously shown to block neurotrophic activity of NGF and NGF loop 1 peptide mimetics in mouse dorsal root ganglion neurons (Longo, F. M., Manthorpe, M., Xie, Y. M., Varon, S. (1997) *J Neurosci Res* 48, 1-17), partially blocked the neurotrophic activity of BDNF (FIG. 3g) and completely blocked the neurotrophic activity of Compounds 3 and 4, while non-immune antibody had no effect. Another independently-derived rabbit polyclonal anti-p75$^{NTR}$ antibody (Ab 9650) gave virtually identical results, p75$^{NTR}$ blockade. Neither of the antibodies produced changes in baseline survival, suggesting that in these cultures the antibody preparations do not promote or inhibit survival. These results are consistent with BDNF acting through both TrkB and p75$^{NTR}$ while NGF and p75-binding compounds act primarily through p75$^{NTR}$.

In addition, the response of p75$^{NTR}$-deficient (−/−) cells to neurotrophins and the p75-binding compounds were examined (FIG. 3h). Baseline survival under these culture conditions was the same in wild type and deficient cells, while p75$^{NTR}$-deficiency was associated with partial responsiveness to BDNF, and lack of response to NGF and the p75-binding compounds, a pattern similar to that found in the p75$^{NTR}$-antibody studies. Finally, treatment with 5 nM Compounds 3 or 4 along with 50 ng/ml NGF, concentrations of each which induce a maximal response, produced no additive effect on survival, further supporting the hypothesis that the p75-binding compounds act directly through binding to p75$^{NTR}$.

Despite the observation that Compounds 3 and 4 did not affect NGF-TrkA/Fc binding, the question remained whether the p75-binding compounds activate TrkB, the principal Trk on the hippocampal neurons, or the nominally expressed TrkA, as their primary mechanism for promoting survival. Also, ligand binding to p75$^{NTR}$ might influence Trk activation. With these considerations, it was of interest to determine whether the p75-binding compounds promote Trk activation. Compounds 3 and 4 were assessed for the ability to activate Trk autophosphorylation, as indicated by Trk$^{Y490}$ phosphorylation, a well-established marker of Trk activation. In hippocampal cultures. BDNF exposure resulted in robust Trk activation (FIG. 3i), while no activation was detected with NGF or the p75-binding compounds. The lack of signal with NGF confirms that these cultures produce little or no TrkA and supports the idea that the trophic effects of NGF are mediated principally by p75$^{NTR}$. In 3T3-TrkA cells, NGF exposure produced the expected TrkA autophosphorylation response, while the p75-binding compounds again showed no activity (FIG. 3j). These results suggested that activation of Trk receptors does not play a primary role in the promotion of cell survival by p75-binding compounds.

Example 4

Compounds Work Through p75$^{NTR}$

Together, the displacement of NGF from p75$^{NTR}$ by the active compounds, but not with an inactive compound, the dependence of biologic function on the presence of an unoccluded p75$^{NTR}$, lack of Trk interactions and activation and lack of additive effects between NGF and compound, strongly suggest that the p75-binding compounds directly interact with and work through p75$^{NTR}$.

This is consistent with the pharmacophoric model used herein to select the p75-binding compounds (FIG. 1). Given fitting to this model as the principal initial selection criterion, the identification of a high percentage of chemically diverse positives from a small group tested in vitro, and their similar actions in a variety of biochemical and biologic assays, the evidence suggests that the p75-binding compounds interact at a p75$^{NTR}$ neurotrophin binding site rather than at other locations in the receptor.

Pro-survival signaling associated with p75$^{NTR}$ actions include activation of P13K and AKT (Roux, P. P., Bhakar, A. L., Kennedy, T. E. Barker, P. A. (2001) *J Biol Chem* 276, 23097-23104; Lachyankar, M. B., et al. (2003) *J Neurosci Res* 71, 157-172), NFκB (Mamidipudi, V., Li, X., Wooten, M. W. (2002) *J Biol Chem* 277, 28010-28018; Carter, B. D., et al. (1996) *Science* 272, 542-545; Gentry, J. J., Casaccia-Bonnefil, P., Carter, B. D. (2000) *J Biol Chem* 275, 7558-7565; Foehr, E. D., et al., (2003) *J Neurosci Res* 73, 7556-7563), and ERK (Lad, S. P., Neet, K. E. (2003) *J Neurosci Res* 73, 614-626). Each of these signaling intermediates has been shown to be capable of being independently regulated by Trk and p75$^{NTR}$ through pathways with varying degrees of overlap and crosstalk, and with different kinetics. Treatment of hippocampal neurons with 20 nM Compounds 3 and 4 (a concentration in the plateau range for acute signaling activation) led to an approximately 1.5 fold increase in NFκB-p65 phosphorylation (FIG. 4a), indicative of activation of the NFκB pathway (Sakurai, H., Chiba, H., Miyoshi, H., Supita, T., Toriumi, W. (1999) *J Biol Chem* 274, 30353-30356), similar in extent and time course to that induced by both neurotrophin proteins.

Compound 5 at the same concentration did not induce NFκB-p65 phosphorylation. Consistent with activation of NFκB by Compounds 3 and 4, a specific peptide inhibitor of NFκB translocation, SN50 (Lin, Y. Z., Yao, S. Y., Veach, R. A., Torperson, T. R., Hawiger, J. (1995) *J Biol Chem* 270, 14255-14258), significantly reduced cell survival promoted by Compounds 3 and 4 and the neurotrophins, with no effect on baseline survival (FIG. 4e).

In studies of AKT activation, Compounds 3 and 4 at 20 nM showed similar degrees of activation to that found with NGF at 30 minutes, while BDNF induced a substantially greater response. In addition, the onset of activation stimulated by the Compounds 3 and 4 was slower than that of NGF (FIG. 4b). Consistent with these findings, the P13 kinase inhibitor LY294002, which inhibits AKT activation, markedly decreased survival in all cases, including baseline survival under conditions of no treatment or exposure to Compound 5 (FIG. 4e).

Investigation of ERK signaling showed that ERK44 activation was induced to a greater extent by the neurotrophins than by the p75-binding compounds (FIG. 4c), which showed a significant but small response. ERK42 activation was more robust overall and greater with BDNF and NGF treatment than with the p75-binding compounds. There was a prominent loss of signal by 30 minutes but with greater persistence of the activated form following BDNF treatment (FIG. 4d). Consistent with the finding of greater ERK activation induced by BDNF compared to NGF and p75-binding compounds, the ERK inhibitor PD98059 significantly decreased BDNF-stimulated survival while it had a small but significant effect on NGF activity, and produced no significant decrease in survival promoted by either Compound 3 or 4 (FIG. 4e).

These observations suggest that unlike NFκB and P13K, ERK activation is not a significant factor in the promotion of survival by the p75-binding compounds. The difference likely relates to the lower levels of ERK activation observed with the p75-binding compounds relative to the protein ligands. P13K activation can promote survival through pathways involving and not involving AKT (Zhang, Y., et al. (2003) *J Neurosci* 23, 7385-7394), and so the essential mechanisms downstream of P13K in this system remain to be determined. The more robust activation of AKT and ERKs by BDNF likely represents the influence of TrkB.

To further examine the relationship between compound-mediated AKT and NFκB activation, and neural survival, compound dose-activation studies were performed (FIGS. 4f; 4g). The results demonstrate that Compound 4 induces activation of both AKT and NFκB over a concentration range of 0.5 nM to 3 nM, which is similar to that required for promotion of survival, and concordant with a role for these signaling mechanisms in mediating compound-induced survival.

Further, it was determined that NGF and compound activation of AKT signaling was completely absent in cultures of p75$^{NTR-/-}$ neurons (FIG. 4h), consistent with the hypothesis that NGF and p75-binding compounds activate AKT survival signaling through P75$^{NTR}$. Together with the evidence for p75$^{NTR}$ dependence of compound-induced survival (FIGS. 3g, 3h), these findings suggest that p75-binding compounds induce survival of hippocampal neurons in culture, at least in part, through interactions with p75$^{NTR}$ that produce activation of survival-promoting signaling pathways involving AKT and NFκB.

Example 5

Compounds 3 and 4 Do Not Promote Cell Death of Mature Oligiodendrocytes, but Inhibit proNGF-Induced Death Though NGF and the p75-binding compounds promoted cell survival in the hippocampal cultures used in the studies herein, liganding of p75$^{NTR}$ by mature NGF or proNGF, has been associated with cell death rather than promotion of survival in certain cell types (Lee, R., Kermani, P. Ten % K. K., Hempstead, B. L. (2001) *Science* 294, 1945-1948; Casaccia-Bonnefil, P., Carter, B. D., Dobrowskv, R. T., Chao, M. V. (1996) *Nature* 386, 716-719). To determine whether the p75-binding compounds disclosed herein promote survival or cause death in systems in which neurotrophins promote cell death, the survival of mature oligodendrocytes treated with p75-binding compounds and proNGF was examined.

Figure 5A:
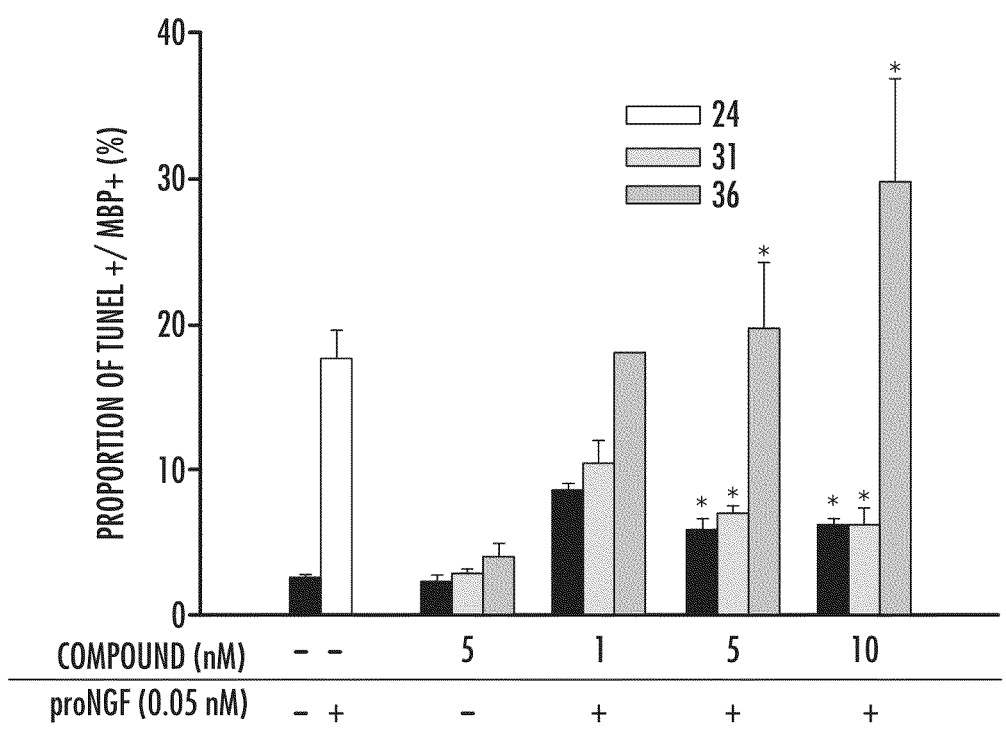
FIG. 5a is a bar graph disclosing that Compounds 3-5 do not promote death of mature oligondendrocytes and inhibits proNGF-induced death. Mature oligondendrocytes were treated as indicated and cell death assessed by determining the proportion of MBP-positive cells that are also TUNEL-positive. In the absence of pro-NGF, compounds did not promote cell death. In the presence of 2.8 ng/ml (0.05 nM) proNGF, Compound 3 and Compound 4, but not Compound 5, blocked cell death. Bars represent mean+s.e.m. n≥2 for each condition except for 1 nM Compound 5 with proNGF which had a single determination. P<0.05, by Student t-test for comparisons with proNGF treatment without compounds. The closed, lighter-shaded, and darker-shaded bars represent Compounds 3, 4, and 5, respectively.

Mature oligodendrocytes express p75$^{NTR}$ but not TrkA, and undergo apoptotic death on treatment with NGF or proNGF (Beattie. M. S., et al. (2002) *Neuron* 36, 375-386; Casaccia-Bonnefil, P., Carter, B. D., Dobrowsky, R. T., Chao, M). (1996) *Nature* 386, 716-719; Yoon, S. O., Casaccia-Bonnefil, P., Carter, B., Chao, M. V. (1998) *J Neurosci* 18, 3273-3281). Unlike NGF or proNGF. Compounds 3, 4, and 5 alone did not promote cell death (FIG. 5a). In addition, proNGF-induced cell death was significantly inhibited by Compounds 3 and 4 over a concentration range of 1 to 10 nM, but not by Compound 5, which appeared to decrease survival at 10 nM (FIG. 5a).

Figure 5B:
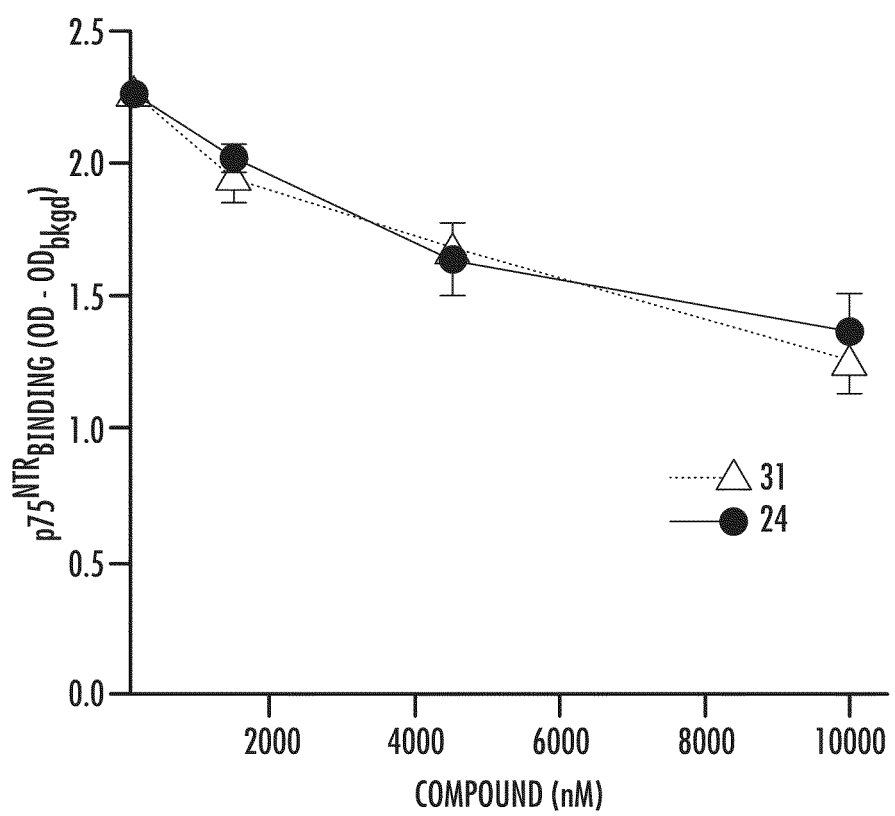
FIG. 5b is a line graph showing proNGF displacement from by Compounds 3 and 4. 100 ng/ml proNGF was incubated with the indicated concentrations of compounds and detected by ELISA. n=4 for each condition. Symbols indicate means+/−s.e.m. The signal from all compound-treated samples were significantly less than proNGF alone, with P<0.01 by Student t-test. The symbols "Δ" and "●" represent Compound 4 and Compound 3, respectively.

In order to determine whether p75-binding compounds block proNGF binding to p75$^{NTR}$, proNGF binding to p75$^{NTR}$ was assessed over a concentration range of 1500 nM to 10,000 nM. Compounds 3 and 4 inhibited proNGF binding equally, up to an approximately 30% decrement at the highest concentration (FIG. 5b). The high concentration required to inhibit pro-NGF binding compared to those blocking proNGF-induced death suggest the possibilities that: 1) in the cell-based assay, with native receptor conformation in the presence of co-receptors (e.g., sortilin), the proNGF-p75$^{NTR}$ interaction may be more susceptible than in the in vitro assay to disruption by the p75-binding compounds; 2) at low concentrations, the compounds qualitatively alter proNGF binding to decrease the induction of cell death, but do not decrease the total amount of proNGF binding to decrease the induction of cell death but do not decrease the total amount of proNGF binding; or 3) that the compounds induce preferential activation of pro-survival signaling by p75$^{NTR}$ without affecting proNGF binding. Preferential survival pathway activation could result from differences in the way the compounds modulate receptor structure, as well as lack of binding to co-receptors expressed by oligodendrocytes, such as sortilin. Indeed, prior studies suggest that engagement of both sortilin and p75$^{NTR}$ by proNGF promotes efficient ligand binding, receptor complex activation and apoptotic actions (Nvkiaer, A., Willnow. T. E., and Petersen, C. M. (2005) *Curr Opin Neurobiol* 15, 49-57).

Example 6

Compound 3 Blocks Aβ-Induced Neural Degeneration

Using previously well established protocols, Aβ was pre-incubated for 3 days in water to allow formation of oligomers. E17 hippocampal neurons were incubated for 5 days to allow for maturation prior to addition of Aβ with test compounds. Mature neurons demonstrate high Aβ vulnerability. Addition of Aβ$_{42-1}$ (30 µM) as a negative control caused no cell death.

Figure 6A:
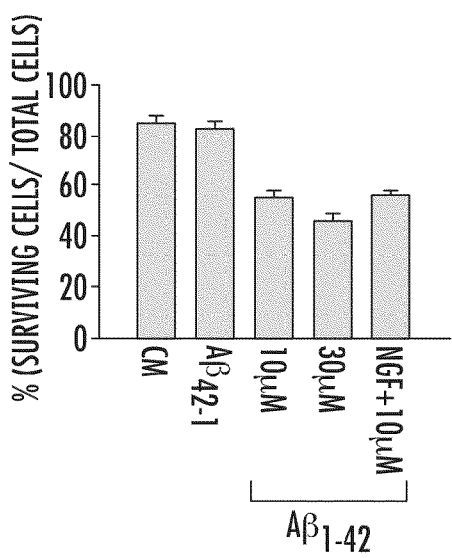
FIG. 6a is a bar graph representing percentage of surviving hippocampal neuronal cells after addition of A$\beta_{1\text{-}42}$ (10 μM or 30 μM). Addition of A$\beta_{1\text{-}42}$ resulted in an approximate 40% loss of neurons after 3 days of exposure. Addition of NGF (100 pg/ml) did not protect against A$\beta_{1\text{-}42}$.

Addition of Aβ$_{1-42}$ at 10 µM or 30 µM caused an approximate 40% loss of neurons after a 3 day exposure (FIG. 6a). The results are similar to in vitro Aβ-induced death levels reported previously (Michaelis. M. L., et al., (2006) *J Pharm Exp Ther* 312:659-668). Addition of NGF (100 pg/ml) fails to protect against Aβ$_{1-42}$, a finding previously reported (Yankner, B. A., et al. (1990) *PNAS* 87:9020-9023).

Figure 6B:
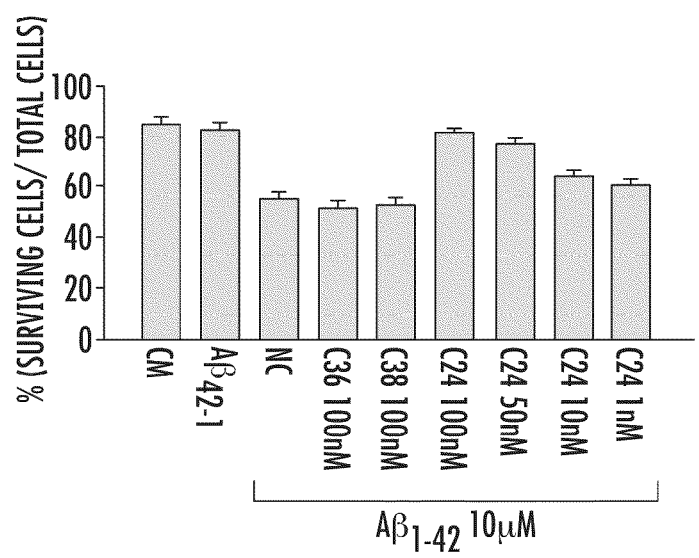
FIG. 6b is a bar graph representing the percentage of surviving hippocampal neural cells after addition of A$\beta_{1\text{-}42}$ (10 μM) with test compounds.

Addition of Aβ$_{1-42}$ in the absence of compound (NC) resulted in a 40% loss of neurons (FIG. 6b). The presence of inactive Compounds 5 and 6 failed to block Aβ$_{1-42}$ toxicity. Addition of Compound 3, however, blocks Aβ-induced death with a dose-response effect and an EC$_{50}$ of approximately 10 nM. Data are expressed as percentage surviving cells over total cells present in a given measurement area. Mean+/−SE is shown with at least 20 areas measured per condition over multiple bioassays. The ability of Compound 4 to entirely block Aβ-induced degeneration at low nanomolar concentrations, its favorable molecular weight (less than 500), and a favorable Lipinski score indicate that it is a high priority lead compound for preclinical development in in vivo AD models. Compound 4 has also been shown to block Aβ-induced degeneration of cortical and septal neurons.

Example 7

Compound 4 Prevents Hair Loss in Middle Aged Mice

In a three-month toxicology trial, the presence of age-related hair loss was demonstrated in 3 of 5 vehicle-treated mice and in 0 of 5 Compound 4-treated male mice. In a follow up study, 4 of 10 vehicle-treated and 0 of 9 Compound 4-treated middle-aged male mice at the 2-month time point demonstrated hair loss.

Taken together, these studies indicate that 7 of 15 vehicle-treated, and 0 of 14 Compound 4-treated mice demonstrate hair loss. The resulting p value is 0.001 (Fisher's Exact test), supporting the presence of a significant effect in the preclinical studies. This data indicates p75$^{NTR}$ regulates the death of hair follicle cells and thereby the process of hair loss (known as catagen). These findings, for the first time, indicate the efficacy of administering small molecule compounds targeting p75$^{NTR}$ for the prevention of hair loss occurring during aging or in pathological states, such as alopecia areata.

Summary of the Examples

In targeting one member of a group of receptors that interact with a given ligand, activation of a subset of receptor-mediated effects which can or can not be naturally occurring was anticipated. Such differences in signaling patterns, including minimizing activation of Trks, will likely prove clinically useful. For example, the compounds disclosed in the Examples can promote survival under conditions where neurotrophins promote death, and can be less likely to induce excessive sympathetic fiber sprouting and upregulation of pain transmission occurring, likely via Trk signaling, with neurotrophin treatments (Walsh, G. S., Krol, K. M., Kawaia, M. D (1999) *J Neurosci* 19, 258-273).

REFERENCES

The references listed below as well as all references cited in the specification are incorporated herein by reference to the extent that they supplement, explain, provide a background for or teach methodology, techniques and/or compounds employed herein.

Appel, S. H. (1981) *Ann Neurol* 10, 499.
Beattie, M. S. et al. (2002) *Neuron* 36, 375-386.
Brann, A. B., et al. (1999) *J Neurosci* 19, 8199-8206.
Bui, N. T., et al. (2002) *J Neurochem* 81, 594-605.
Carter, B. D., et al. (2002) *Science* 272, 542-545.
Casaccia-Bonnefil, P., Carter, B. D., Dobrowsky, R. T., Chao, M. V. (1996) *Nature* 386, 716-719.
Clark, D. E. (2002) *J Pharm Sci* 88, 815-821.
Fahnestock, M., Michalski, B., Xu, B., Coughlin, M. D. (2001) *Mol Cell Neurosci* 18, 210-220.
Foehr, E. D., et al., (2003) *J Neurosci Res* 73, 7556-7563.
Freireich et al., (1966) *Cancer Chemother Rep.* 50, 219-244.
Fu, X. C., Chen, C. X., Liang, W. Q., Yu, Q. S. (2001) *Acta Pharmacol Sin* 22, 663-668.
Gentry, J. J., Casaccia-Bonnefil, P., Carter, B. D. (2000) *J Biol Chem* 275, 7558-7565.
Harrington, A. W. et al. (2004) *Proc Natl Acad Sol USA* 101, 6226-6230.
Harrington, A. W, Kim, J. Y., Yoon, S. O. (2002) *J Neurosci* 22, 156-166.
He, X. L., Garcia, K. C. (2004) *Science* 304, 870-875.
Huang, C. S. et al. (1994) *J Biol Chem* 274, 36707-36714.
Huber, L. J., Chao, M. V. (1995) *Dev Bio* 167, 227-238.
Lachyankar, M. B., et al. (2003) *J Neurosci Res* 71, 157-172.
Lad, S. P., Neet, K. E. (2003) *J Neurosci Res* 73, 614-626.
Lee, K. F. et al. (1992) *Cell* 69, 737-749.
Lee, R., Kermani, P., Teng, K. K., Hempstead, B. L. (2001) *Science* 294, 1945-1948.
Lin, Y. Z., Yao, S. Y., Veach, R. A., Torgerson, T. R., Hawiger, J. (1995) *J Biol Chem* 270, 14255-14258.
Lipinski, C. A. (2000) *J Pharm Toxicol Methods* 44, 235-249.
Longo, F. M. et al. (1999) *J Neurosci Res* 55, 230-237.
Longo, F. M., Manthorpe, M., Xie, Y. M., Varon, S. (1997) *J Neurosci Res* 48, 1-17.
Lutz, M., and Kenakin, T. (1999) *Quantitative Molecular Pharmacology and Informatics in Drug Discovery* (Hoboken, N.J.: John Wiley & Sons).
Maliartchouk, S., Debeir, T., and Beglova, N. Cuello, A. C., Gehring, K. and Saragovi, H. U. (2000) *J Biol Chem* 275, 9946-9956.
Mamidipudi, V., L$_1$, X., Wooten, M. W. (2002) *J Biol Chem* 277, 28010-28018.
McDonald, I, Thornton, J. M., (1994) *WWW Edition December* 1994.

Michaelis, M. L., Ansar, S., Chen, Y., Reiff, E. R., Seyb, K. I., Nimes, R. H., Audus, K. L., and Georg, G. I. (2006) *J Pharm Exp Ther* 312:659-668.

Motulsky, H. J., and Christopoulos, A. (2003) *A Practical Guide to Curve Fitting*, 2$^{nd}$ edn. (San Diego, Calif., GraphPad Software, Inc.).

Neubig, R. R., Spedding, M, Kenakin, T., and Christopoulos, A. (2003) *Pharmacol Rev* 55, 597-606.

Nykjaer, A. et al., (2004) *Nature* 427, 843-848.

Nykjaer, A., Willnow, T. E, and Petersen, C. M. (2005) *Curr Opin Neurobiol* 15, 49-57.

Partridge, W. M. (2002) *Adv Exp Med Bio* 513, 397-430).

Podulso, J. F., Curran, G. L. (1996) *Brain Res Mol Brain Res* 36, 280-286.

Remington: The Science and Practice of Pharmacy, A. Gennaro, ed., 20th edition, Lippincott, Williams & Wilkins, Philadelphia, Pa.

Remington's Pharmaceutical Sciences, Mack Pub. Co., Easton, Pa., 1980.

Roux, P. P., Bhakar, A. L., Kennedy, T. E., Barker, P. A. (2001) *J Biol Chem* 276, 23097-23104.

Sakurai, H., Chiba, H., Miyoshi, H., Sugita, T., Toriumi, W. (1999) *J Biol Chem* 274, 30353-30356.

Salehi, A. H., et al. (2000) *Neuron* 27, 279-288.

Saltzman, W. M., Mak, M. W, Mahoney, M. J., Duenas, E. T., Cleland, J. L. (1999) *Pharm Res* 16, 232-240.

Walsh, G. S., Krol, K. M., Kawaja, M. D. (1999) *J Neurosci* 19, 258-273.

Wang, J. J., Rabizadeh, S., Tasinato, A., Sperandio, S., Ye, X., Green, M., Assa-Munt, N., Spencer, D., and Bredesen, D. E. (2000) *J Neurosci Res* 60, 587-593.

Yang, T. et al. (2003) *J Neurosci* 23, 3353-3363.

Yankner, B. A., Caceres, A., Duffy, L. K. (1990) *PNAS* 87:9020-9023.

Yoon, S. O., Casaccia-Bonnefil, P., Carter, B., Chao, M. V. (1998) *J Neurosci* 18, 3273-3281.

Zhang, Y., et al. (2003) *J Neurosci* 23, 7385-7394.

Zhou, J., Holtzman, D. M., Weiner, R. I., Mobley, W. C (1994) *Proc Natl Acad Sci USA* 91, 3824.

Zhou, J., Valletta, J. S., Grimes, M. L., Mobley, W. C (1995) *J Neurochem* 65, 1146-1156.

It will be understood that various details of the presently claimed subject matter can be changed without departing from the scope of the presently claimed subject matter. Furthermore, the foregoing description is for the purpose of illustration only, and not for the purpose of limitation.

What is claimed is:

1. A pharmaceutical formulation comprising a unit dose of an active ingredient and a pharmaceutical grade carrier, wherein said active ingredient is selected from the group consisting of a compound having the structure:

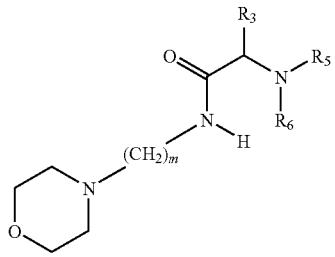

wherein:
   m is an integer from 1 to 8;
   $R_3$ is selected from the group consisting of H, alkyl, cycloalkyl, halo, hydroxyl, alkoxyl, aryloxyl, and aralkyloxyl; and
   $R_5$ and $R_6$ are each independently selected from the group consisting of H, alkyl, cycloalkyl, aryl, hydroxyl, alkoxyl, hydroxyalkyl, hydroxycycloalkyl, alkoxycycloalkyl, aminoalkyl, acyloxyl, alkylaminoalkyl, and alkoxycarbonyl;
or a pharmaceutically acceptable salt thereof.

2. A pharmaceutical formulation comprising a unit dose of an active ingredient and a pharmaceutical grade carrier, wherein said active ingredient is a compound having the structure:

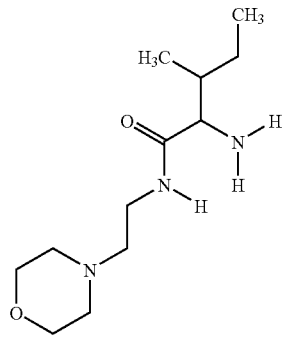

Compound 4 or a pharmaceutically acceptable salt thereof.

3. The pharmaceutical formulation of claim 1, wherein said formulation is a liquid solution, suspension, emulsion, tablet, pill, or capsule.

4. The pharmaceutical formulation of claim 3, formulated for administration to a human.

5. The pharmaceutical formulation of claim 2, wherein said formulation is a liquid solution, suspension, emulsion, tablet, pill, or capsule.

6. The pharmaceutical formulation of claim 5, formulated for administration to a human.

* * * * *